(12) United States Patent
Rai et al.

(10) Patent No.: US 11,112,405 B1
(45) Date of Patent: Sep. 7, 2021

(54) ASSAY DEVICE, SYSTEM, METHOD, AND KIT

(71) Applicant: Baseline Global, Inc., Irvine, CA (US)

(72) Inventors: Balwant Rai, Dragor (DK); Jeffery Floyd McAllister, Monona, WI (US); Peter Andrew Smith, Cary, NC (US); Jay Colton Zignego, Bahama, NC (US); Michael Eugene O'Donnell, Sussex, WI (US); Leonard Kristal, Berkeley, CA (US); Matthew Hon Ming Kwok, Irvine, CA (US); Mark Kin Ming Kwok, Irvine, CA (US)

(73) Assignee: Baseline Global, Inc., Irvine, CA (US)

( * ) Notice: Subject to any disclaimer, the term of this patent is extended or adjusted under 35 U.S.C. 154(b) by 0 days.

(21) Appl. No.: 17/075,481

(22) Filed: Oct. 20, 2020

Related U.S. Application Data

(63) Continuation of application No. PCT/US2020/033365, filed on May 18, 2020.

(51) Int. Cl.
*G01N 33/543* (2006.01)
*B01L 3/00* (2006.01)
*G01N 33/558* (2006.01)

(52) U.S. Cl.
CPC ...... *G01N 33/54386* (2013.01); *B01L 3/5023* (2013.01); *G01N 33/558* (2013.01);
(Continued)

(58) Field of Classification Search
None
See application file for complete search history.

(56) References Cited

U.S. PATENT DOCUMENTS 6,187,598 B1   2/2001   May et al.
7,029,627 B2   4/2006   Alley
(Continued)

FOREIGN PATENT DOCUMENTS

EP   2836844   10/2013
MX   358474    8/2018
(Continued)

OTHER PUBLICATIONS

PCT/US2020/33365 International Search Report and Written Opinion of the International Searching Authority, dated Aug. 17, 2020.
(Continued)

*Primary Examiner* — Rebecca M Giere
(74) *Attorney, Agent, or Firm* — Jansson Munger McKinley & Kirby Ltd.

(57) ABSTRACT

Assay devices, systems, methods, and kits useful for detection of analytes in a bodily fluid sample, such as saliva, are disclosed herein. Assay devices may include a fluid sample collector and an assessment unit to which the fluid sample collector couples. The fluid sample collector may include a cap with a plunger and absorbent member that collects a bodily fluid sample. Insertion of the plunger into the assessment unit during coupling provides pressure-driven fluid flow through a filter rapidly delivering bodily fluid filtrate to one or more test panels which provide the assay result. In embodiments, an on-board light source enables a user to readily detect changes in a test panel indicative of the presence of an analyte thus providing an opportunity for obtaining rapid results with improved confidence.

26 Claims, 11 Drawing Sheets

(52) U.S. Cl.
CPC ..... *B01L 2200/10* (2013.01); *B01L 2300/025* (2013.01); *B01L 2300/042* (2013.01); *B01L 2300/069* (2013.01); *B01L 2300/0636* (2013.01); *B01L 2300/0663* (2013.01); *B01L 2300/0681* (2013.01); *B01L 2400/0487* (2013.01)

(56) References Cited

U.S. PATENT DOCUMENTS

| | | | |
|---|---|---|---|
| 7,695,953 | B2 | 4/2010 | Gould et al. |
| 7,837,939 | B2 | 11/2010 | Tung et al. |
| 7,879,293 | B2 | 2/2011 | Niedbala et al. |
| 7,879,623 | B2 | 2/2011 | Guirguis |
| 7,927,562 | B2 | 4/2011 | Wan et al. |
| 8,313,644 | B2 | 11/2012 | Harris et al. |
| 8,326,412 | B2 | 12/2012 | Goldstein et al. |
| 8,551,016 | B2 | 10/2013 | Slowey et al. |
| 8,603,008 | B2 | 12/2013 | Libby et al. |
| 8,632,680 | B2 | 1/2014 | Hermansson et al. |
| 8,728,329 | B2 | 5/2014 | Ellis et al. |
| 8,871,155 | B2 | 10/2014 | Wu et al. |
| 9,198,641 | B2 | 12/2015 | Slowey et al. |
| 9,414,813 | B2 | 8/2016 | Engel et al. |
| 9,529,002 | B2 | 12/2016 | Rai et al. |
| 9,927,445 | B2 | 3/2018 | Rai et al. |
| 9,964,550 | B2 | 5/2018 | Sanders |
| 10,023,903 | B2 | 7/2018 | Wong et al. |
| 10,035,146 | B2 | 7/2018 | Fuller et al. |
| 10,234,452 | B2 | 3/2019 | Benson |
| 10,739,335 | B2 | 8/2020 | Harel |
| 2005/0119589 | A1 | 6/2005 | Tung et al. |
| 2007/0128070 | A1 | 6/2007 | Wu et al. |
| 2007/0244368 | A1 | 10/2007 | Bayloff et al. |
| 2008/0199851 | A1* | 8/2008 | Egan ............... B01L 3/5029 435/5 |
| 2010/0137741 | A1 | 6/2010 | Slowey et al. |
| 2010/0331725 | A1 | 12/2010 | Libby et al. |
| 2011/0165024 | A1 | 7/2011 | Wu et al. |
| 2012/0148458 | A1 | 6/2012 | Benson |
| 2012/0295281 | A1 | 11/2012 | Rai et al. |
| 2013/0157381 | A1* | 6/2013 | Pang ............... G01N 33/53 436/501 |
| 2014/0072982 | A1 | 3/2014 | Rai et al. |
| 2015/0153366 | A1 | 6/2015 | Sanders |
| 2016/0011183 | A1 | 1/2016 | Egan et al. |
| 2017/0067913 | A1 | 3/2017 | Rai et al. |
| 2018/0003723 | A1 | 1/2018 | Rai et al. |
| 2018/0038852 | A1 | 2/2018 | Manuguerra et al. |
| 2018/0106799 | A1 | 4/2018 | Brenner et al. |
| 2018/0143187 | A1 | 5/2018 | Henkin |
| 2018/0235206 | A1 | 8/2018 | Laughlin et al. |
| 2018/0284139 | A1 | 10/2018 | Rai et al. |
| 2018/0321251 | A1 | 11/2018 | Beckley |
| 2019/0053744 | A1 | 2/2019 | Janigro et al. |
| 2019/0078982 | A1 | 3/2019 | Whiteside, Jr. |
| 2019/0128813 | A1 | 5/2019 | Clarke et al. |
| 2020/0003772 | A1 | 1/2020 | Harel et al. |
| 2020/0013488 | A1 | 1/2020 | Lui et al. |

FOREIGN PATENT DOCUMENTS

| | | |
|---|---|---|
| WO | 2007062575 | 6/2007 |
| WO | 2013153461 | 10/2013 |
| WO | 2020110143 | 6/2020 |

OTHER PUBLICATIONS

PCT/US2020/040701 International Search Report and Written Opinion of the International Searching Authority, dated Oct. 2, 2020.

Oasis Diagnostics Our Products, https://4saliva.com/products/, Oasis Diagnostics Corporation, Vancouver, WA 98686, Downloaded from the Internet Apr. 2, 2020.

Infectious Disease Testing, www.orasure.com/products-infectious/index. html, OraSure Technologies, Inc., Bethlehem, PA 18015, Downloaded from the Internet Dec. 3, 2020.

OraQuick Advance HIV, www.orasure.com/products-infectious/OraQuick-Advance-HIV/html, OraSure Technologies, Inc., Bethlehem, PA 18015, Downloaded from the Internet Dec. 3, 2020.

Statswab oral drug tests, Directions for use, http://www.drugteststrips.com/, DrugTestStrips.com, Greenville, South Carolina, 29606, Downloaded from the Internet Apr. 8, 2020.

Onsite Oral 7 Saliva Drug Test, https://www.onsitedrugtesting.com.au/oral-7, Onsite Diagnostics Pty. Limited, Manly Vale, NSW, Australia, 2093, Downloaded from the Internet Apr. 8, 2020.

Saliva Drug Test Kit Rapid Detect SDS 10 Panel, https://rapiddetect.com/product/sds-10-panel-saliva-drug-test-kit/, Rapid Detect, Inc., Poteau, OK 74953, Downloaded from the Internet Apr. 8, 2020.

Flexible Smartphone Lateral Flow Reader Customization, www.abingdonhealth.com/contract-services/lateral-flow-reader/appdx/.com, Abingdon Health, York, UK, Downloaded from the Internet Apr. 14, 2020.

Detekt Biomedical L.L.C., Rapid Test Readers for the Analysis of Lateral Flow and Dry Chemistry Strips, and Detekt quantitative reader Product Description, www.iDetekt.com, Detekt Biomedical L.L.C., Austin, TX 78744, Downloaded from the Internet Apr. 14, 2020.

Mehta et al., COVID-19: Consider Cytokine Storm Syndromes and Immunosuppression, Lancet, vol. 395: 1033-1034 (2020) (DOI:10.1016/S0140-6736(20)30630-9).

* cited by examiner

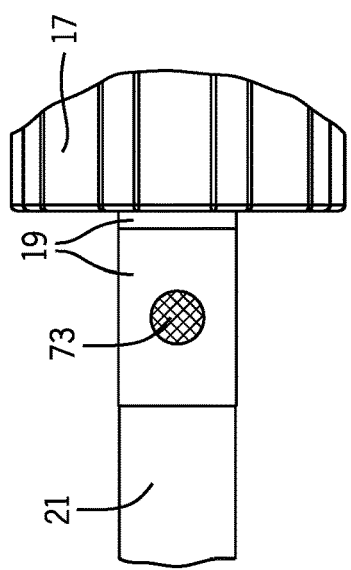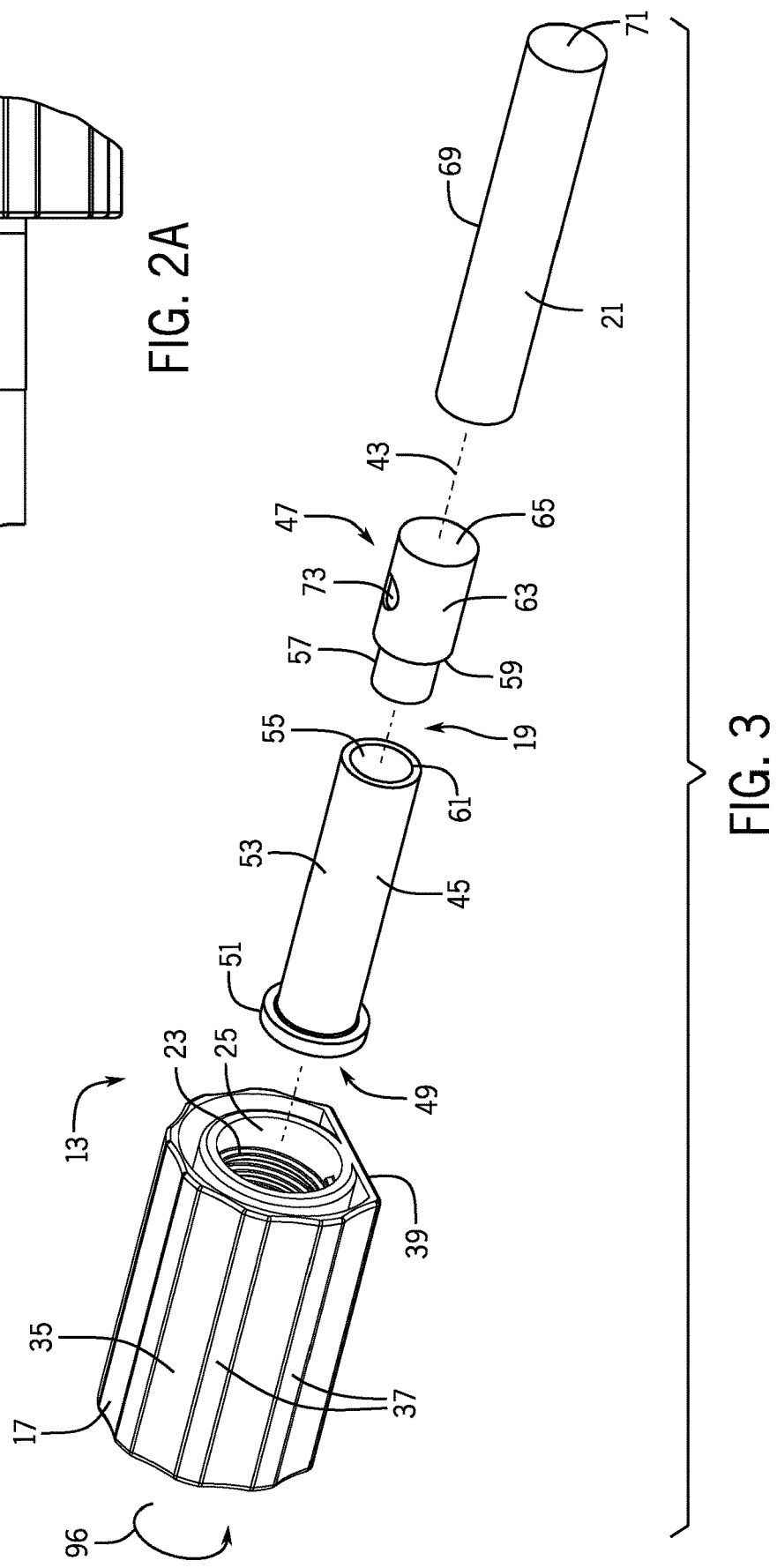

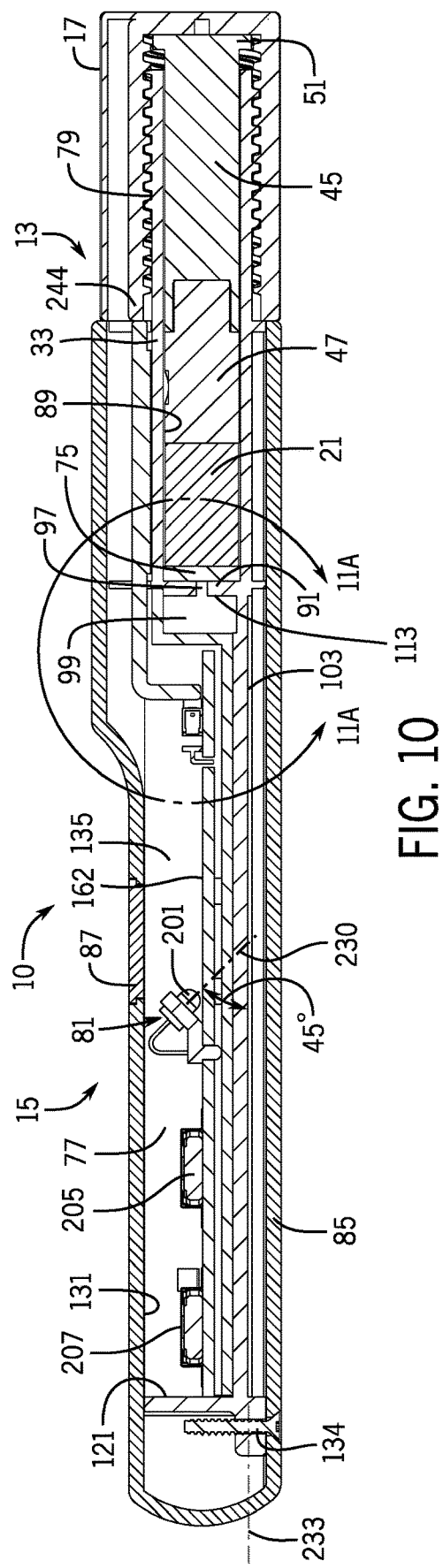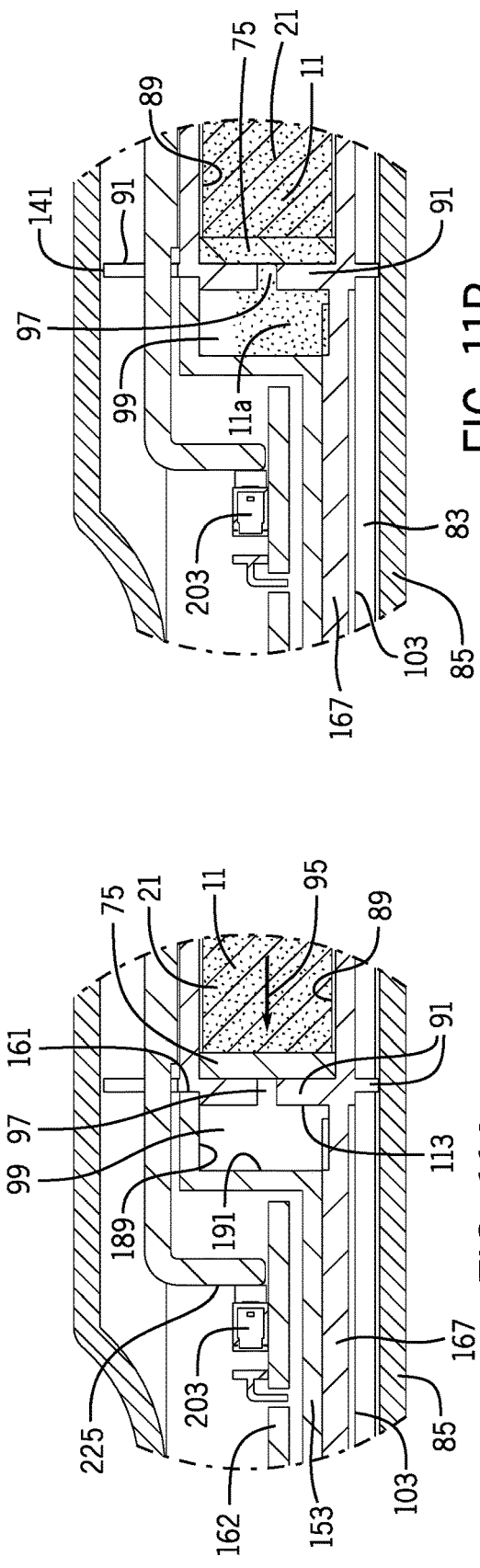

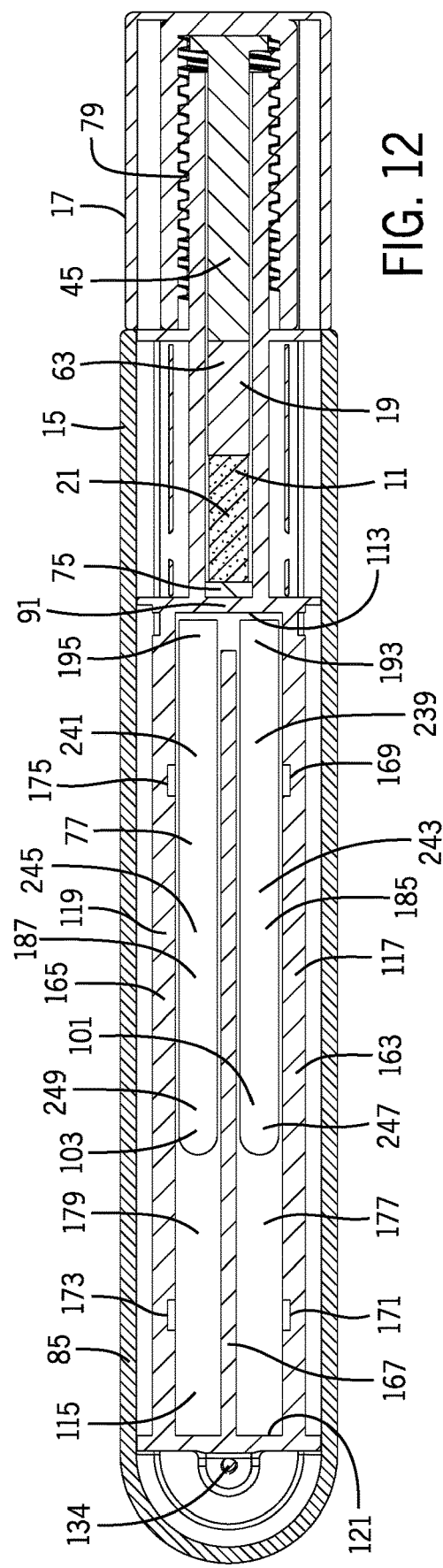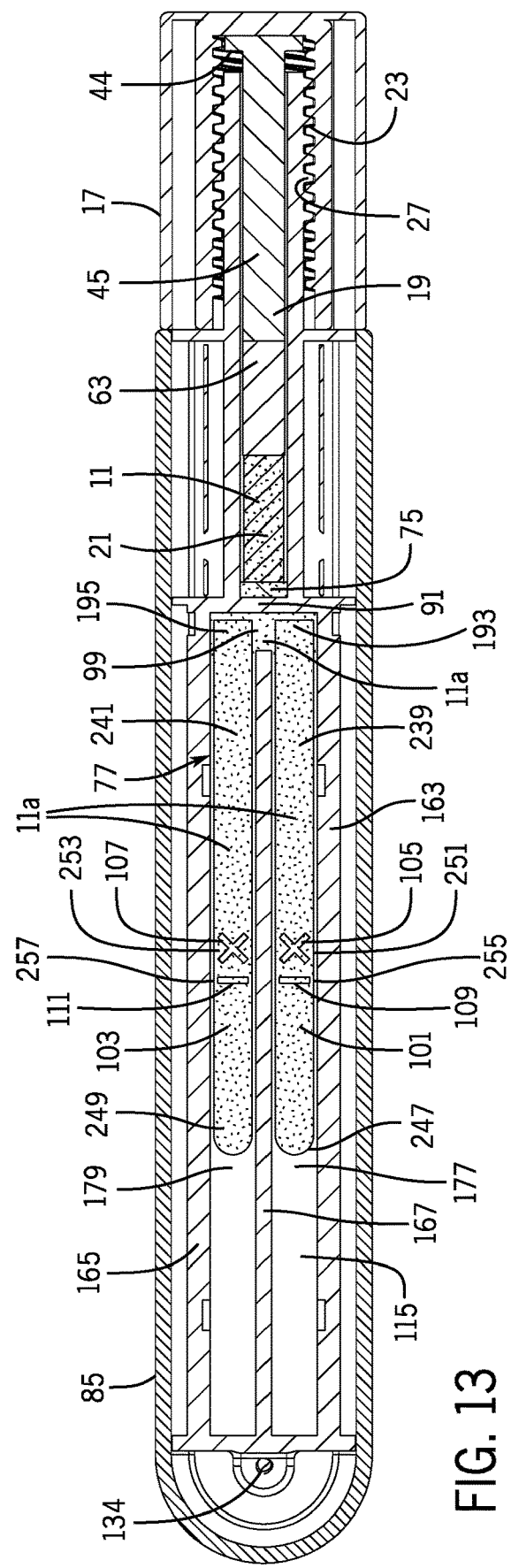

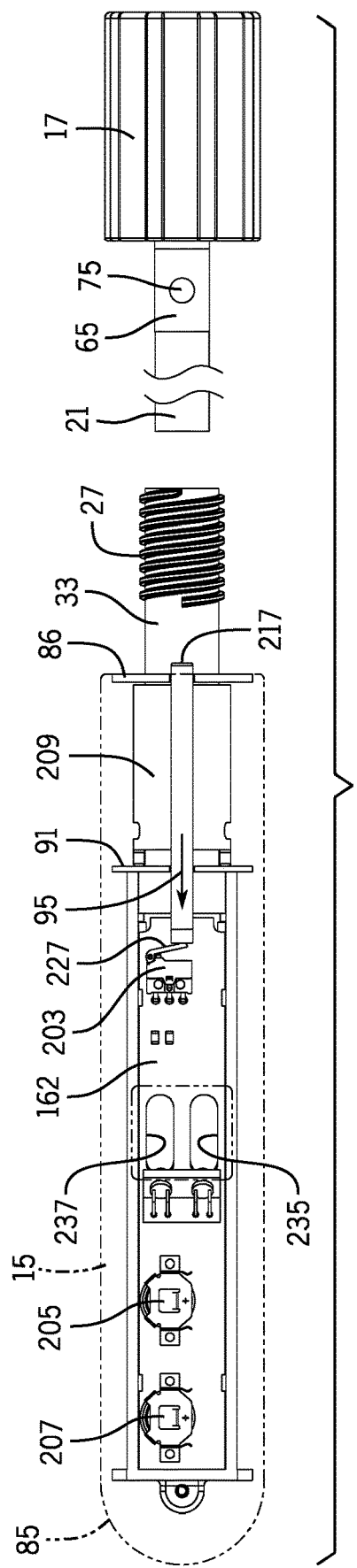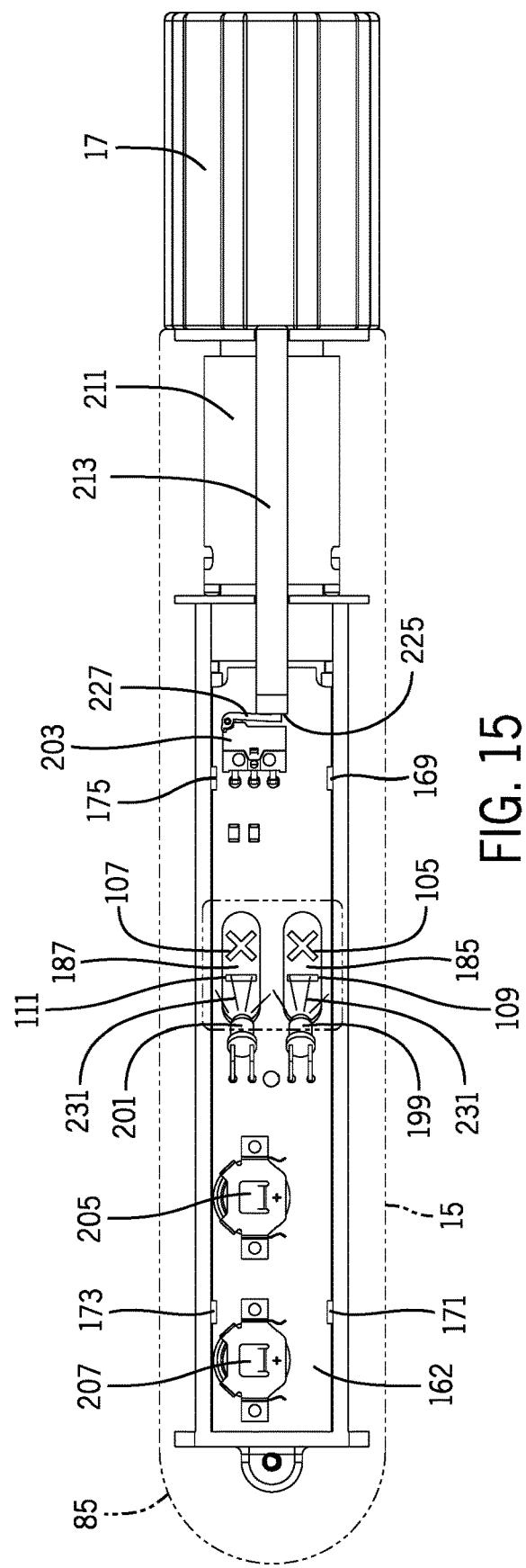

ASSAY DEVICE, SYSTEM, METHOD, AND KIT

RELATED APPLICATION

This application is a continuation of international patent application Serial No. PCT/US2020/033365 filed with the United States Patent & Trademark Office as PCT Receiving Office on May 18, 2020 and designating the United States. The entire content of international patent application Serial No. PCT/US2020/033365 is incorporated herein by reference for continuity.

FIELD

The present invention relates to point-of-care assay devices, systems, methods, and kits useful for detection of analytes in a bodily fluid sample.

BACKGROUND

Analytes in bodily fluid taken from a subject are known to provide important health-related information. Examples of bodily fluid may include saliva, urine, tears, perspiration and blood. Analytes present in bodily fluid may be any molecule or target of interest, such as proteins, carbohydrates, nucleic acids, and ribonucleic acids. By way of example only, information obtained through detection and/or measurement of such analytes can be used for important purposes such as to diagnose disease, to evaluate whether a subject has been exposed to viral and other pathogens, to determine the existence and severity of traumatic brain injury (TBI) in a subject, and for other purposes.

A number of devices exist for the collection and testing bodily fluids to determine the presence or absence of analytes in such bodily fluids. These devices may include a fluid sample collector and a testing device. The fluid sample collector may incorporate some sort of absorbent material. In the case of devices used to test saliva samples, the absorbent material may be placed directly in the subject's mouth. The sample is subsequently removed from the absorbent material and transferred to the testing device.

A typical testing device for detecting analytes in the fluid sample may include a lateral flow test strip. A typical lateral flow test strip is composed of four main elements, namely, a sample pad, a conjugate release pad, a lateral flow membrane with test and control lines, and a backing pad. These components are typically enclosed within a testing device housing. The result provided by the lateral flow test strip is indicative of the presence or absence of the analyte.

While existing assay devices for detecting analytes in bodily fluid may be satisfactory for their intended purpose, there is an important need for improvement. For example, existing assay devices can require excessive time within which to provide a result indicative of whether the analyte is, or is not, present. Time-to-result can be important when rapid diagnosis of a condition is necessary, such as with a subject who may have sustained a concussion. Excessive time can be required both with respect to time to deliver bodily fluid to a lateral flow test strip and to visualize the indication provided by the lateral flow test strip.

Existing assay devices may be suboptimal with respect to potential accuracy of the result. With such devices, there may be an opportunity for adulteration of the lateral flow test strip negatively affecting the assay result. Moreover, it may be difficult to visualize the result provided by the lateral flow test strip, particularly in assays with low concentrations of analyte.

In addition, it is important that any point-of-care assay device be simple and intuitive to use. Simplicity of use is important so that persons of varying levels of medical skill can easily use the assay device and confidently interpret the results provided by the assay device with respect to whether the analyte is, or is not, present in the bodily fluid.

There is a need for improved devices, systems, methods, kits, and other techniques and discoveries for detection of analytes in a bodily fluid, which would provide assay results rapidly, which would produce accurate assay results capable of being understood immediately and with confidence, which could be used at a point-of-care or where otherwise needed to quickly and accurately provide information about the condition and/or health of a subject, which would be easy and intuitive to use by people of varying skill levels, which would be relatively inexpensive providing an opportunity for a single-use disposable assay device, and which would generally provide opportunities for better healthcare.

SUMMARY

The invention relates to assay devices, systems, methods, and kits useful for detection of analytes in a bodily fluid sample. The invention may be implemented at a point-of-care, a point-of-injury or wherever needed. Assay devices as described herein are useful for detection of analytes in bodily fluids such as saliva, urine, tears, perspiration, and blood. Analytes present in bodily fluid may be any molecule or target of interest, such as proteins, carbohydrates, nucleic acids, and ribonucleic acids. Use of assay device embodiments with saliva is particularly useful because saliva can be obtained easily and non-invasively from a subject and saliva is a known carrier of analytes, such as proteins, which are known to be indicative of conditions in a subject, such as TBI. Assay devices as described herein may be adapted for use in performing assays seeking to detect a broad range of different types of analytes and analyte combinations to thereby identify many different types of conditions in a wide range of subjects including men, women, adults, children, and, potentially, animals.

Assay devices, systems, methods and kits according to the invention provide an opportunity to obtain rapid and accurate assay results which are capable of being immediately understood with certainty by essentially any adult. Assay devices according to the invention and systems, methods, and kits incorporating the assay devices provide an opportunity for an elegant assay device which essentially "informs" the user with respect to how to use the device and which can be produced inexpensively enabling the device to be discarded after a single use.

In embodiments, an assay device for detection of an analyte in a bodily fluid sample may comprise a fluid sample collector and an assessment unit. The fluid sample collector and assessment unit are removably coupled together and can be supplied to the user packaged or unpackaged in a fully or partially coupled state to provide sterility of the assay device components prior to use for an assay.

A representative fluid sample collector may be designed for collection of any bodily fluid but has particular utility with gathering saliva samples because absorbent member of the collector may be placed directly in the subject's mouth to collect saliva thereon. A fluid sample collector may include a cap, a plunger carried by the cap and the aforementioned absorbent member may be supported toward a distal end of the plunger. The absorbent member may be compressible and may be a sponge in certain embodiments. The plunger may include a moisture indicator in fluid communication with the absorbent member which produces an indication when a sufficient volume of bodily fluid is on the absorbent member for testing.

A representative assessment unit is provided to receive a bodily fluid sample transferred from the fluid sample collector when the assessment unit and collector are partially or fully coupled together. One test panel or plural test panels of the assessment unit may then provide an indication with respect to whether one or more analyte of interest is, or is not, present in the bodily fluid. In embodiments, the indication may also be indicative of the concentration of analyte in the bodily fluid.

In embodiments, an assessment unit may include a sample-receiving chamber with an opening into which the absorbent member and plunger are inserted for the fluid transfer. A fluid filter component of assessment unit removes particulates and impurities from pressurized bodily fluid driven from the sample-receiving chamber by means of positive displacement provided by the plunger. The filtrate flows through a fluid outlet in sample-receiving chamber. Preferably, the fluid outlet is a port in an end wall of the sample-receiving chamber and the filter is across the port. A well (i.e., a receiving space), of assessment unit is provided to receive purified filtrate from the filter. At least one test panel receives filtrate from the well for purposes of performing an assay.

In embodiments, threads removably couple the fluid collector cap to the assessment unit closing the opening. Rotation of the cap during coupling advances the plunger within the sample-receiving chamber to provide the aforementioned pressure which drives fluid flow through the filter and filtrate into the well. A window which may optionally be covered with a transparent panel, may be provided in the assessment unit permitting user viewing of the indication(s), or lack of indication(s) provided by each test panel.

In embodiments, the plunger and the sample-receiving chamber in which the plunger is advanced serve as a type of positive displacement device which builds pressure within sample-receiving chamber and across the filter to drive fluid flow through the filter speeding delivery of filtrate to the well and test panel(s) thereby providing for a more rapid assay and shorter time to the assay result. In such embodiments, the plunger and absorbent member supported by plunger provide positive displacement in the same manner as piston advancement in a cylinder. The pressure may drive fluid flow through the filter and through the preferred fluid outlet port preferably provided in an end wall. In such embodiments, the filter may be across the port to remove particulates from the bodily fluid that might adulterate and invalidate the assay. In embodiments, the axial advancement of the plunger may create a pressure within the sample-receiving chamber of about 40 kPa. (Kilopascal) to about 200 kPa (Kilopascal), a pressure range of about 5.8 PSI (pounds per square inch) to about 29 PSI (pounds per square inch).

The filter may be selected to provide optimal particle removal based on the bodily fluid being assayed. In embodiments, the filter may be a hydrophilic membrane, a hydrophobic membrane, or a membrane including both hydrophilic and hydrophobic elements. Sizing of the pores of the filter may also be selected to provide optimal particle removal and may include a range of pores from about 0.1 µm (micron) to about 120 µm (micron) depending on the size of the particulates to be removed.

The assay device may be configured for use with conventional lateral flow test strip applications. The assessment unit may include a test chamber and the well and the at least one test panel may be within the test chamber. One test panel, or plural test panels may be implemented. Each test panel may be of a material which wicks fluid filtrate from the well and across the panel. Each test panel may be adapted for detection of one analyte or a plurality of analytes. A symbol may be indicated on the test panel if the target analyte is present. A further symbol may be indicated if a sufficient volume of fluid filtrate is present on the test panel to ensure a valid assay.

In certain embodiments, the assay device may include an onboard light source to provide visualization of the indication(s) provided by each test panel. Preferably, the onboard light source is a part of, and within, the assessment unit. In embodiments, advancement of the cap during cap rotation and coupling may serve to activate the light source. Componentry for the light source, including the light source, a switch for the light source, and a power source, may be elements of a printed circuit board within the assessment device.

In embodiments, the light source may cause fluorescence of a label associated with the analyte. The light source may emit at least ultra violet (UV) light. UV light emitted by the light source may be in the range of about 200 nm to about 350 nm, although other ranges may be implemented. The light source may be at an angle relative to the test panel which may be about 30° to about 50° relative to the test panel. The light source improves visualization of the indication provided by each test panel at analyte concentrations of about 0.1 picogram of analyte per 1 milliliter of filtrate (1 pg analyte/ml filtrate) or greater meaning that very minute indications can be more easily and confidently be visualized by the user.

Therefore, and in embodiments, the single act of coupling the fluid sample collector with assessment unit triggers operation of multiple aspects of the assay device including delivery of bodily fluid to the assessment unit from the absorbent member of the fluid collection device and pressure-driven fluid flow and filtration of the bodily fluid for rapid delivery to the test panel or panels speeding commencement of the assay. The coupling may also automatically activate the light source to enable the user to immediately visualize changes to the test panel(s) as well as to visualize indications provided by the test panel(s) indicative of analyte concentrations which would be otherwise imperceptible with a human eye providing confidence regarding whether the analyte is, or is not, present in the bodily fluid.

These and other embodiments and specific and possible advantages will become evident with reference to the following description.

BRIEF DESCRIPTION OF THE DRAWINGS

Examples of assay devices and systems, methods and kits utilizing such devices may be understood by reference to the following description taken in conjunction with the accompanying drawings, in which like reference numerals identify like elements throughout the different views. The drawings are not necessarily to scale, emphasis instead being placed upon illustrating the principles of the invention.

In the accompanying drawings:

FIG. 2A illustrates a plunger and moisture indicator taken along detail section 2A-2A of FIG. 2;

FIG. 3 is an exploded view of a fluid sample collector;

FIG. 10 is a section view of the assay device of FIG. 1 taken along section 10-10 of FIG. 8 showing the fluid sample collector and assessment unit portions coupled together;

FIG. 11A is an enlarged view taken along detail section 11A-11A of FIG. 10 illustrating an absorbent member compressed within the assessment unit and showing the direction of pressurized bodily fluid flow toward a filter;

FIG. 11B is an enlarged view also taken along detail section 11A-11A of FIG. 10, but illustrating filtration of contaminants from the bodily fluid and passage of fluid filtrate through the filter and into a well;

FIG. 12 is a section view of the assay device of FIG. 1 taken along section 12-12 of FIG. 9 illustrating test panels in the form of lateral flow test strips in a first state;

FIG. 13 is a section view of the assay device of FIG. 1 taken along section 12-12 of FIG. 9, but illustrating the lateral flow test strips in a second state saturated with bodily fluid and providing visible indications;

FIG. 14 illustrates light source and circuit components internal to the assay device of FIG. 1;

FIG. 15 illustrates light source and circuit components internal to the assay device of FIG. 1, but showing operation of the light source to improve visualization of indications on the test panels.

DETAILED DESCRIPTION

As illustrated in FIGS. 1-16, the present invention relates to improved assay devices 10 for detection of analytes in bodily fluids 11 and to systems, methods, and kits for use and implementation of said assay devices 10. Assay devices 10 of the types described herein enable analysis of bodily fluids such as saliva, urine, tears, perspiration, and blood for the presence of analytes indicative of health-related conditions such as disease (e.g., Alzheimer's and/or Parkinson's disease), exposure to pathogen(s), and the existence of injury, such as concussion. Analytes which may be detected with assay device 10 may include any molecule or target of interest, such as proteins, carbohydrates, nucleic acids, and ribonucleic acids which may be present in bodily fluid 11.

Assay devices 10 of the types described herein are capable of providing highly accurate and easily understood information at, for example, a point-of-care, a point-of-injury, or wherever needed. The assay devices 10 may be provided as an elegant self-contained unit for reasons of sterility and intuitive ease-of-use and may be inexpensively produced as a lightweight, portable unit capable of a single use and of being discarded after such use, if desired. Assay devices 10 are particularly useful with bodily fluids 11 such as saliva and urine because of the ease and non-invasiveness of collection of such fluids. Accordingly, assay devices 10 of the types described herein are capable of broad distribution and use to rapidly provide health-related information about many different health conditions to thereby enable better healthcare decisions and provide opportunities for improved healthcare results.

Figure 1:
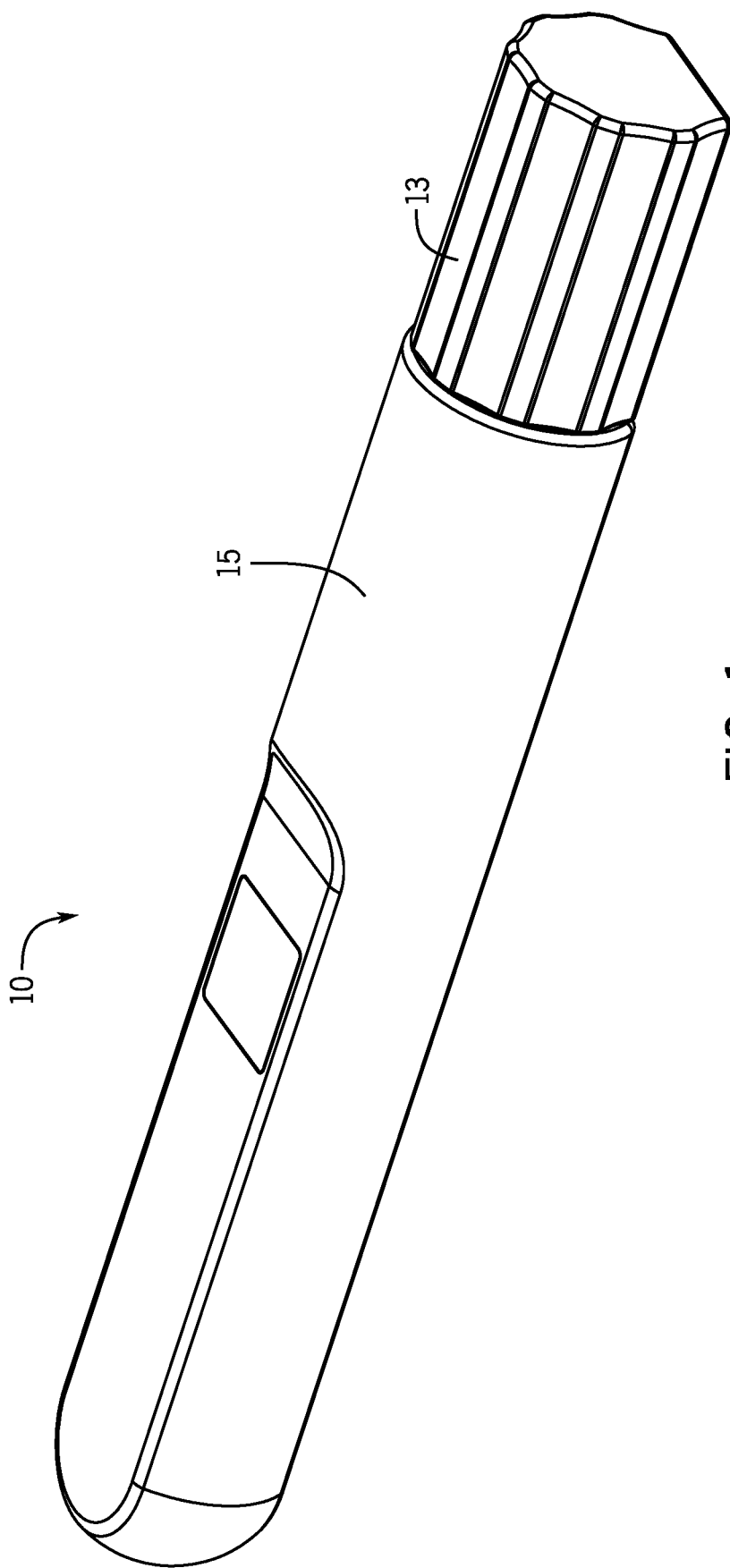
FIG. 1 is a perspective view of an embodiment of an assay device according to the invention showing fluid sample collector and assessment unit portions coupled together.

Referring then to FIGS. 1-16, an assay device 10 may comprise a fluid sample collector 13 and an assessment unit 15. Embodiments of assay device 10 may be provided for storage, distribution, and pre-use in the form of an elegant self-contained unit as illustrated in FIG. 1 with fluid sample collector 13 fully or partially coupled to assessment unit 15. Pre-use coupling of fluid sample collector 13 with assessment unit 15 provides an opportunity to protect components internal to assay device 10 from contact with contaminants prior to use. Such coupling further provides for intuitive use in which it can be easily understood that the fluid sample collector 13 and assessment unit 15 are decoupled for sample collection and then reassembled to perform the assay. Therefore, coupling as used herein may include both complete and partial coupling of fluid sample collector 13 with assessment unit 15.

Referring to FIGS. 1-3 and 5-16, a fluid sample collector 13 capable of use with assay device 10 may include a cap 17, a plunger 19, and an absorbent member 21. Absorbent member 21 may be compressible as illustrated in the embodiments. In the embodiments, cap 17 may couple fluid sample collector 13 to assessment unit 15 by means of connecting threads 23 within barrel 25 internal to cap 17. Threads 23 may mesh and mate with corresponding receiving threads 27 on an outer surface 29 of side wall 31 of sample-receiving chamber 33 as described in further detail herein. A thread refers to a helical structure to allow two parts to be screwed together. Threads 23, 27 convert rotational movement to linear movement and force. Cap 17 may be considered coupled to assessment unit 15 once threads 23, 27 are meshed and cap 17 may be considered fully coupled when it can no longer be advanced on threads 23, 27. While threads 23 and 27 are illustrated as internal and external threads respectively, it is to be understood that this thread arrangement could be reversed.

Optionally, a locking device, such as a locking pawl, could be provided to prevent removal of cap 17 once it is fully advanced on threads 23, 27 and fully coupled with assessment unit 15. Such a locking pawl would be desirable to prevent removal of cap 17 and fluid sample collector 13 from assessment unit to thereby prevent contact from contaminates outside of assay device 10 during or after an assay.

Cap 17 may include an outer surface 35 with a plurality of raised axial elongate ribs generally radially disposed around cap 17, several of which are indicated by reference number 37. Ribs 37 may be provided to ensure positive gripping and manipulation of cap 17 by means of a user's thumb and forefinger. Cap 17 outer surface 35 may further include a flattened portion 39 which may be aligned with a corresponding flattened portion 41 on assessment unit 15 when cap 17 is fully seated on sample-receiving chamber 33.

If provided, flattened portions 39, 41 collectively provide a generally flat bottom surface for assay device 10, thereby enabling assay device 10 to be set upright on a flat surface (e.g., a table, a bench, etc.) free of any rolling movement during performance of an assay.

Figure 2:
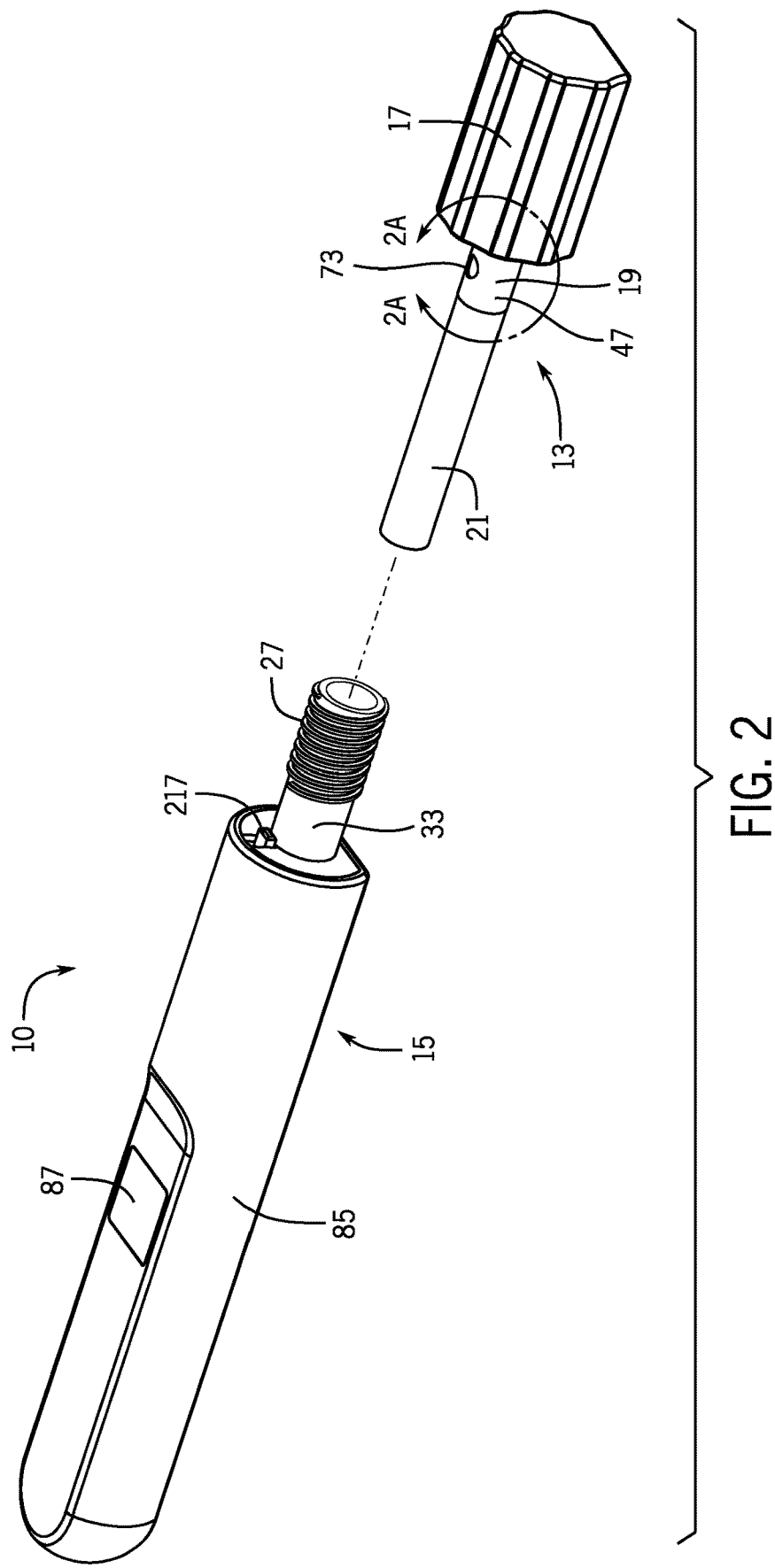
FIG. 2 is a further perspective view of the assay device of FIG. 1 showing the fluid sample collector and assessment unit portions decoupled from one another.
Figure 7:
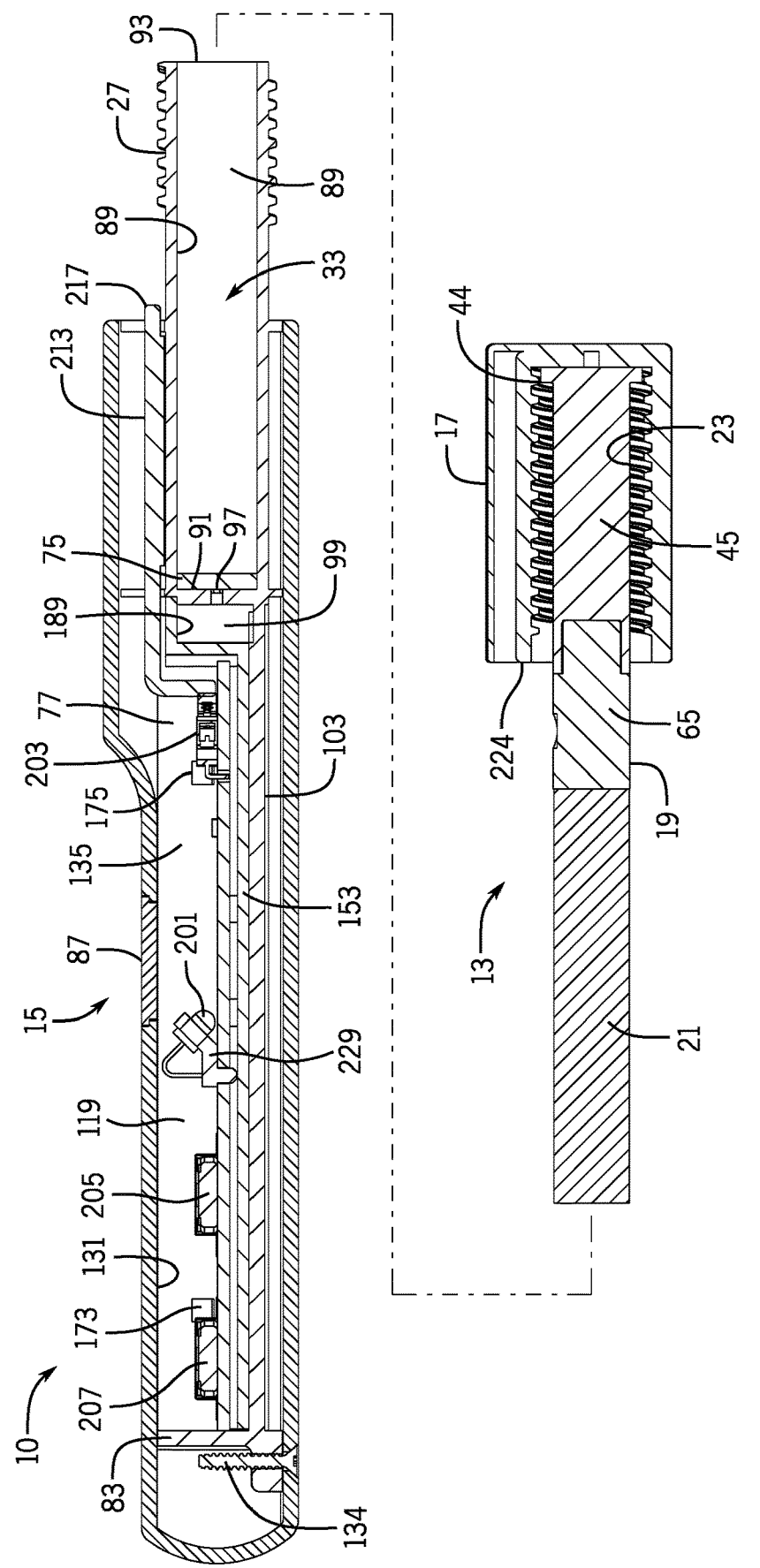
FIG. 7 is a section view of the assay device of FIG. 1 taken along section 7-7 of FIG. 5 showing the fluid sample collector and assessment unit portions decoupled from one another.
Figure 8:
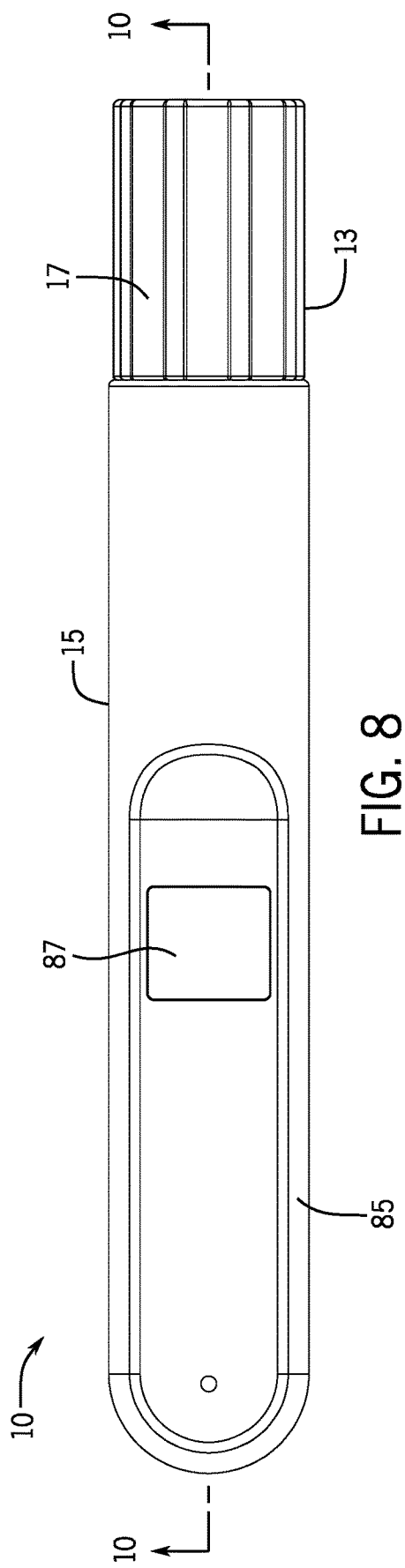
FIG. 8 is a top side of the assay device of FIG. 1 showing the fluid sample collector and assessment unit portions coupled together.
Figure 9:
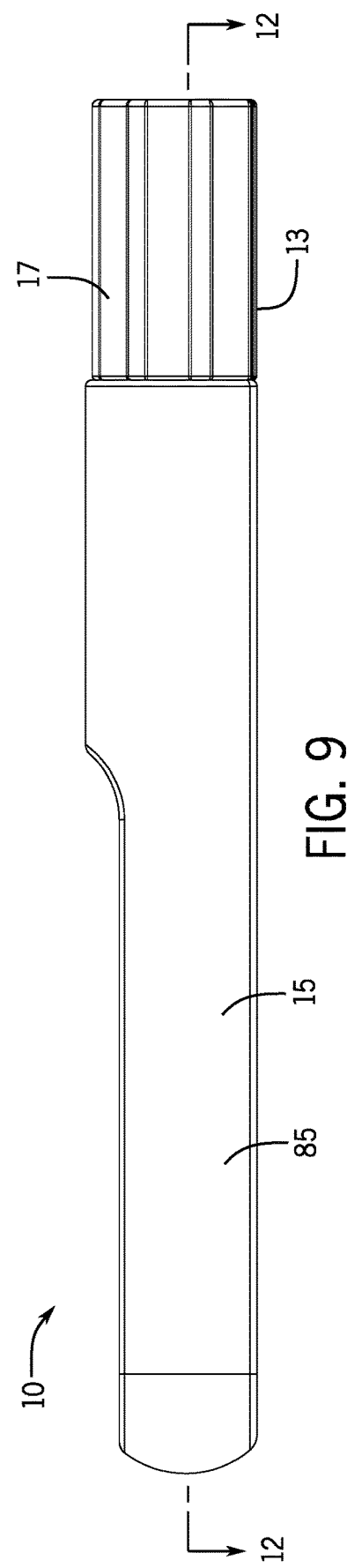
FIG. 9 is a side view of the assay device of FIG. 1 showing the fluid sample collector and assessment unit portions coupled together.

Referring to FIGS. 2-3 and 7, cap 17, plunger 19, and absorbent member 21 may be coaxially disposed along fluid collector axis 43. Plunger 19 may include a base 45 and a moisture indicator 47 joined to base 45. Base 45 and moisture indicator 47 of plunger 19 may be of a rigid material, such as a hard plastic material. A proximal end 49 of plunger 19 may include a flange 51 radially outward from plunger sidewall 53. Plunger 19 may be inserted into barrel 25 of cap 17 so that flange 51 can snap fit within retainer 44 (FIG. 7) of barrel 25 to rigidly attach to cap 17 extending outward from cap 17 along axis 43. Plunger 19 is carried by cap 17 by virtue of the snap fit. In embodiments, plunger 19 may float with respect to cap 17 so that cap 17 may rotate independent of plunger 19.

As illustrated in FIG. 3, base 45 sidewall 53 may define a hollow space 55 which provides a receiver for post 57 of moisture indicator 47 inserted therein. Post 57 may be held on base 45 with surface 59 abutting and resting on distal end 61 of base 45 by any suitable means, such as a friction fit and/or adhesive. Moisture indicator 47 may include a housing 63 extending to a distal end 65 of plunger 19. Accordingly, in the examples, plunger 19 is supported by cap 17 and extends outward from cap 17 to distal end 65.

Referring to FIGS. 2-3, 5-7, and 10-14, absorbent member 21 may be joined to and supported by moisture indicator 47 component of plunger 19. Plunger 19 and absorbent member 21 may have outer surfaces 67, 69 and be of a generally cylindrical configuration. Absorbent member 21 may extend to a distal end 71. Plunger 19 and absorbent member 21 may have a common single diameter normal to axis 43. Absorbent member 21 is preferably of compressible material for reasons which will become apparent. Absorbent member 21 may be made of any suitable material capable of holding a bodily fluid sample (e.g., saliva, urine, etc.) Absorbent member 21 is preferably of a compressible material. Examples are a sponge, a pad, a swab, and combinations of these types of absorbent parts. Suitable materials may include polyester, polyurethane, vegetal cellulose, cellulose, nylon, rayon, silicone, and cotton.

Referring now to FIGS. 2, 2A, and 3, moisture indicator 47 housing 63 may enclose an indicator material 73, such as a di-chromic material, which undergoes a color change or other change detectable with a human eye when exposed to moisture, such as a bodily fluid (e.g., saliva, urine, etc.). Bodily fluid 11 may diffuse, wick, or otherwise migrate into housing 63 and onto indicator material 73 once absorbent member 21 receives bodily fluid 11 from a subject. Indicator material 73 may change color or appearance once bodily fluid 11 is received by indicator material 73 in a volumetric amount sufficient to ensure a valid assay. The state change of indicator material 73 may be from a first state in which no moisture or insufficient moisture is present (FIGS. 2, 3, and 5) and a second state (FIG. 2A) which differs from the first state, to indicate to the user that a volumetric amount of bodily fluid 11 sufficient for a valid assay is present on absorbent member 21. The state change may be indicated by a color change or any other change detectable by human eyesight.

In the examples, plunger 19 including base 45 and moisture indicator 47, and absorbent member 21 are inserted into sample-receiving chamber 33 by manipulation of cap 17 with the user's thumb and forefinger. Once inside sample-receiving chamber 33 (FIGS. 1, 8-13, and 16), bodily fluid 11 may be transferred to assessment unit 15 from fluid sample collector 13 for purposes of an assay as described in further detail herein. Cap 17 and plunger 19 may be made of lightweight plastic materials.

Turning next to FIGS. 1, 2, and 4-16, embodiments of an assessment unit 15 capable of performing an assay when coupled with fluid sample collector 13 to receive a fluid sample 11 therefrom will next be described. According to the embodiments, an assessment unit 15 may include sample-receiving chamber 33, filter 75, test chamber 77, and threads 27 which mate with cap 17 threads 23 in the example, and an onboard light source 81. In the examples, mating threads 23, 27 comprise connector structure 79. Test chamber 77 may comprise test chamber inner casing 83 enclosed within housing 85 of assessment unit 15. Casing 83 is received inside housing to form an enclosed test chamber 77 in the examples. Test chamber wall 86 joined to housing 85 closes test chamber 77 shielding it from contact by contaminants. Onboard light source 81 may be located within test chamber 77 of assessment unit 15. A transparent panel 87 be provided in housing 85 through which to view the assay results provided within test chamber 77 of assessment unit 15 as described herein.

Figure 4:
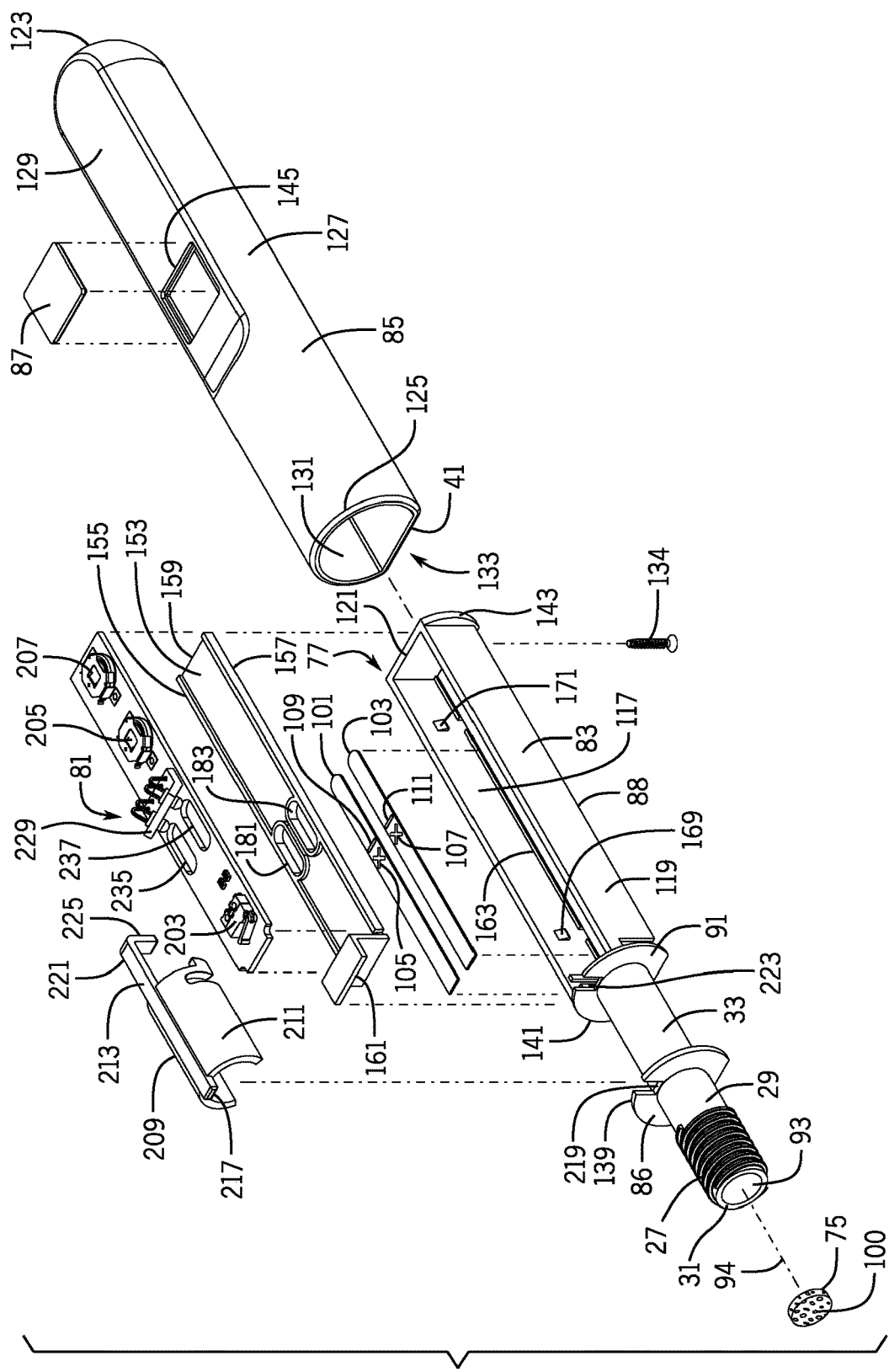
FIG. 4 is an exploded view of an assessment unit.
Figure 5:
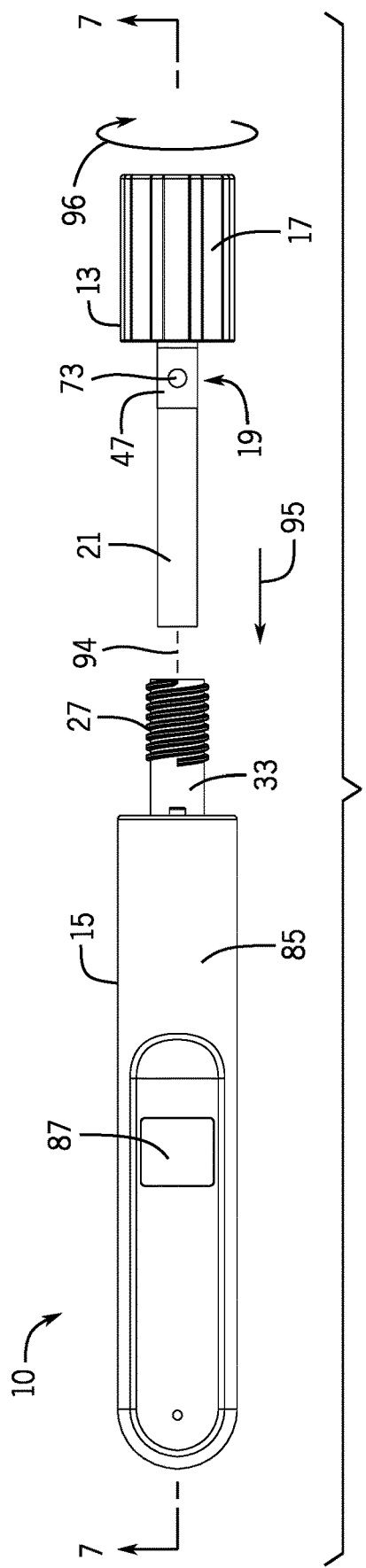
FIG. 5 is a top side view of the assay device of FIG. 1 showing the fluid sample collector and assessment unit portions decoupled from one another.
Figure 6:
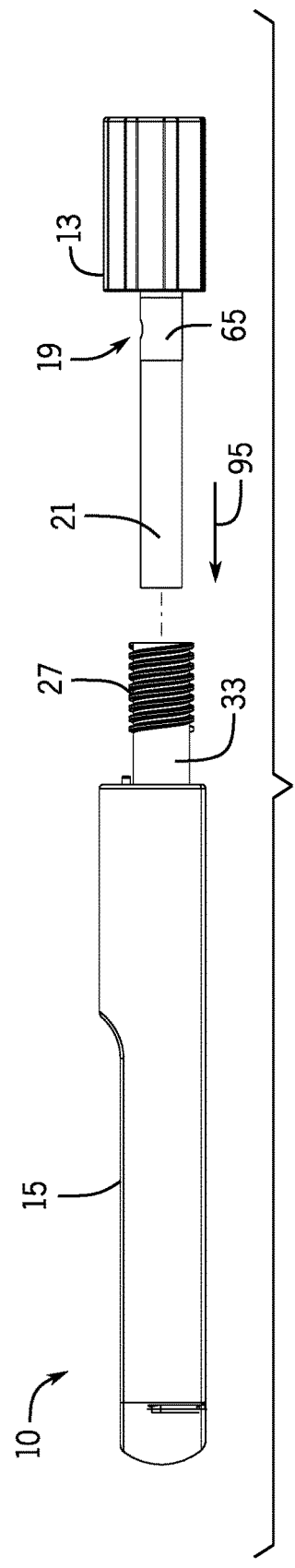
FIG. 6 is a side view of the assay device of FIG. 1 showing the fluid sample collector and assessment unit portions decoupled from one another.

Referring now to FIGS. 1-2 and 4-16, sample-receiving chamber 33 and casing 83 of test chamber 77 may be provided as a one-piece component 88 as in the exploded diagram of FIG. 4. By way of example only, sample-receiving chamber 33 and casing 83 may be provided as a one-piece component 88 in the form of a unitary plastic part.

In the examples, sample-receiving chamber 33 may include a tubular side wall 31 having outer 29 and inner 89 surfaces, an end wall 91, and a chamber opening 93. Side 31 and end 91 walls may define a cylindrical sample-receiving chamber 33 with a chamber axis 94. Opening 93 may be sized to receive plunger 19 and absorbent member 21 inside sample-receiving chamber 33 such that fluid sample collector axis 43 may be coaxial with chamber axis 94.

In the examples, side wall 31 defines a sample-receiving chamber 33 with a cylindrical cross-sectional shape. In other embodiments, sample-receiving chamber 33 could be of any suitable cross-sectional shape, such as a rectangle or a triangle, defined by plural side walls.

Referring to the examples of FIGS. 2, 4-7 and 10-14, the cylinder defined by side 31 and end 91 walls may be sized to have an inside diameter which closely approximates the outside diameter of plunger 19 and absorbent member 21. In such embodiments, plunger 19 functions as a piston within a cylinder provided by inner surfaces 89 of sample-receiving chamber 33. The sizing may be such that outer surfaces 67, 69 of plunger 19 and absorbent member 21 touch or are closely proximate to inner surface 89 of side wall 31 to form a fluid-tight seal therebetween. The sizing should be such that pressure is increased within sample-receiving chamber 33 when plunger 19 is moved axially toward end wall 91 in the direction of arrow 95. Appropriate gaskets or O-rings may be provided to aid in providing a fluid-tight seal between plunger 19 and inner surface 89 of side wall 31. Accordingly, plunger 19 within sample-receiving chamber 33 serves as a positive displacement device for driving bodily fluid flow 11 by means of fluid pressure as described herein. Further and as illustrated in FIGS. 10-13, distal end 71 of absorbent member 21 may be sized such that it is compressed against end wall 91 and inner surface 89 of side wall 31 by plunger 19 when cap 17 of fluid collector 13 is fully coupled with assessment unit 15 and plunger 19 is advanced in the direction of arrow 95. The aforementioned pressure increase and compression may be for purposes of rapid bodily fluid 11 transfer as described herein.

Plunger 19 may be advanced axially within fluid-receiving chamber 33 in the direction of axial arrow 95 by rotation of cap 17 in the direction of rotational arrow 96 (FIGS. 3 and 5) and engagement of mating threads 23, 27. Rotation of cap 17 also advances cap 17 in the direction of arrow 95. The pitch of threads 23, 27 may be selected to advance plunger 19 by the desired axial amount. By way of non-limiting example only, the pitch of threads 23, 27 may be selected to advance plunger 19 with absorbent member 21 thereon by about 5 min for each complete 360° rotation of cap 17 on assessment unit 15 with about six complete 360° rotations required to fully seat cap 17 on assessment unit 15. In such an embodiment, plunger 19 with absorbent member 21 would have about 30 mm travel in the direction of arrow 95 to advance plunger 19 to build pressure within sample-receiving chamber 33 and to compress and press absorbent member 21 against end wall 91 expressing fluid 11 under pressure.

Referring to FIGS. 4, 7, and 10-13, assay device 10 may advantageously be provided with a pressure-type filtration system to rapidly and positively remove impurities and contaminants from bodily fluid 11. Impurities and contaminants that could be in a saliva sample may consist of a broad range of substances such as food, tobacco, mucous, microorganisms (e.g., bacteria), and medications. The impurities and contaminants may, for example, consist of micro-particles having particle size diameters of about 0.1 μm or greater. Removal of impurities and contaminants from bodily fluid 11 is important to ensure that any assay performed with the assay device 10 is accurate and not adulterated. Further, provision of purified bodily fluid 11 filtrate 11a as rapidly as possible contributes to an earlier assay result. In the embodiments, bodily fluid 11 flows under pressure through filter 75 providing for more rapid removal of a greater amount of impurities and contaminants than is possible with filtration by any wicking action or diffusion where no pressure is applied.

Referring to the section views of FIGS. 7 and 10-11B, it can be seen that a fluid port 97 may be provided entirely through end wall 91 of sample-receiving chamber 33. Port 97 is a type of fluid outlet. The fluid outlet provided by port 97 enables bodily fluid 11 to flow from sample-receiving chamber 33 and into test chamber 77 for holding in well 99 of test chamber 77. While one port 97 is illustrated, it should be understood that any number and arrangement of ports may be implemented and port 97 may be located in walls other than end wall 91 in other embodiments. Port 97 may have a reduced cross-sectional area as compared with the cross-section of sample-receiving chamber 33 and end wall 91.

In the examples, a fluid filter 75 is provided across port 97 for purposes of removing impurities and contaminants from bodily fluid 11. A pressure differential exists across filter 75 with high pressure on the side of filter 75 facing sample-receiving chamber 33 and lower pressure on an opposite side of filter 75. Filter 75 may be provided with a plurality of small pores 100, or openings, through filter 75. Such pores 100 enable bodily fluid 11 to flow through filter 75 while particles larger than the pores 100 are stopped at the surface of the filter 75. Such a filtration process is ideal for the batch-type filtration which occurs when a volume of bodily fluid 11 is expressed in a batch from absorbent member 21 into sample-receiving chamber 33 under pressure provided by axial movement of plunger 19 within sample-receiving chamber 33 in the direction of arrow 95. Filter 75 may be at any suitable location to block and remove impurities and contaminants prior to delivery of the bodily fluid 11 in the form of filtrate 11a to test chamber 77 and may be located in or on (i.e., associated with) end wall 91 of sample-receiving chamber 33 across port 97. Filter 75 may be secured in any suitable manner, such as by a press fit, by sonic welding, or by adhesive.

Filter 75 may be referred to as a "microfilter". A microfilter may be a membrane having a pore 100 size or size range of about 0.1 μm to about 1.20 μm. In embodiments, the pore 100 size range of the filter may be about 0.1 μm to about 10 μm. In other embodiments, the pore 100 size range of the filter 75 may be about 0.5 μm to about 1 μm. A pore 100 size range of about 0.5 μm may be highly desirable in assay device 10 embodiments based on saliva as the bodily fluid 11. Filter 75 may, for example, comprise a hydrophilic membrane, or a hydrophobic membrane, or a membrane comprising both hydrophilic and hydrophobic materials. Filter 75 may be of materials selected for a given application of assay device 10. Examples of materials suitable for use as filter 75 may include polyvinylidene difluoride (PVDF), polytetrafluoroethylene (PTFE), polypropylene, acrylic copolymer, polyethersulfone, and other suitable materials or material combinations. Sources of filter 75 may include Whatman® FP and GF/C grade filters. Whatman brand filters are types of high-efficiency filters that will retain fine particles at 90-99% efficiency.

In other embodiments, end wall 91 could be removed or reduced in size such that a port or fluid outlet is provided by an open end of sample-receiving chamber 33. In such embodiments, filter 75 could be held across such fluid outlet by suitable means such as a circumferential ridge or indentation along inner surface 89 of sample-receiving chamber 33. Such a filter 75 may be a rigid filter or have a rigid support (e.g., a screen) in such embodiments. Axial movement of plunger 19 in the direction of arrow 95 would increase pressure within sample-receiving chamber 33 because of the small pore 100 size(s) relative to the fluid volume to aid in speeding up filtration and filtrate 11a delivery to well 99 and test panels 101, 103.

As will be described in more detail herein, bodily fluid 11 flows under pressure through filter 75. In the embodiments, the positive displacement device provided by plunger 19 axially advancing within sample-receiving chamber 33 creates a pressure differential across filter 75 with high pressure on the chamber 33 side of filter 75 and lower pressure on the well 99 side of filter 75 causing bodily fluid 11 to flow under pressure through filter 75 removing small contaminants (e.g., greater than 0.1 μm or greater than 0.5 μm) to yield filtrate 11a. In addition, pressing of absorbent member 21 within sample-receiving chamber 33 and against side and end walls 31, 91 to compress absorbent member 21 expresses bodily fluid 11 therefrom and through filter 75. Expressing, as used herein, means or refers to the pressing out of bodily fluid 11 from a carrier which may be absorbent member 21. The force applied to absorbent member 21 by plunger 19 and side and end walls 31, 91 may occur as fluid sample collector 13 is coupled with assessment unit 15 as explained herein to create the pressure which acts on the bodily fluid 11. By way of example only, a representative pressure may be between about 40 kPa to about 200 kPa, a pressure range of about 5.81 PSI to about 29 PSI.

Referring to FIGS. 4, 7, and 10-15, test chamber 77 may be provided for purposes of enclosing one or more test panel 101, 103 within casing 83. As explained in more detail below, test panels 101, 103 may be of a type commonly referred to as a lateral flow strip assay (LFSA). In such LFSA test panels 101, 103, capillary action of LFSA test panels 101, 103 wicks bodily fluid 11 across the strips to produce an indication 105, 107 (X-shaped symbol "X") and 109, 111 (a bar-shaped symbol "---") (FIGS. 13, 15-16) when contacted by an analyte in bodily fluid 11, and/or by labels in the bodily fluid filtrate 11*a* itself. Test panels 101, 103 may be in fluid communication with well 99 so that bodily fluid filtrate 11*a* diffuses from well 99 onto test panels 101, 103 for purposes of an assay as explained herein. While two test panels 101, 103 are illustrated in the examples, it is to be understood that any number of test panels may be implemented. Furthermore, assays other than LFSA based on test panels 101, 103 may be implemented. And, indications 105, 107, 109, 111 other than X-shaped symbols or bars may be implemented.

In the examples, casing 83 for holding test panels 101, 103 may be provided as part of the one-piece part 88 including sample-receiving chamber 33. Casing 83 may provide a sort of tub-like structure within which test panels 101, 103 may be held for purposes of an assay. Casing 83 may be an axial elongate enclosure coaxial with and sharing chamber axis 94. Casing 83 may include an inner side 113 of end wall 91, and bottom 115, side 117, 119, and distal end walls 121. Test panels 101, 103 may lie against bottom side 115 of casing 83 surrounded by end 91, 12.1 and side 117, 119 walls.

In the embodiments, sample-receiving chamber 33 and test chamber 77 may each share end wall 91. As mentioned previously, port 97 may extend entirely through shared end wall 91 to allow bodily fluid 11 to flow from sample-receiving chamber 33, through filter 75, and into test chamber 77 putting sample-receiving chamber 33 and test chamber 77 in fluid communication with each other. The tub-like structure illustrated in the examples is capable of holding any free or excess bodily fluid filtrate 11*a* which might be present within casing 83.

Exemplary housing 85 may be provided to (1) provide an enclosed test chamber 77, and (2) to provide a means for easily holding and manipulating assessment unit 15 and assay device 10 with a user's hand. In the examples, housing 85 may be provided in the form of an elongate semi-cylindrical hollow tube sealed at one end and open on the other. More specifically, housing 85 may have distal 123, and proximal 125 ends, a wall 127 with outer and inner surfaces 129, 131 and a space 133 within housing 85 bounded by wall 127 inner surface 131. Distal end 123 of housing 85 may be closed and proximal end 125 may define an opening 133 through which the unitary part 88 including sample-receiving chamber 33 and casing 83 are received within space 135. Fastener 134 may be provided to secure unitary part 88 including sample-receiving chamber 33 and casing 83 to housing 85 within space 135. As previously described, housing wall 127 may include generally flat bottom surface 41 with which the flat bottom surface 39 of the cap 17 of fluid sample collector 13 may align when cap 17 is fully seated on assessment unit 15 to enable assay device 10 to rest without movement on a table, bench, or other flat surface during performance of an assay. Closed distal end 123 may be tapered. Housing 85 may be of lightweight plastic material.

Referring to FIGS. 2 and 4 in particular, test chamber wall 86 may be provided to seal test chamber 77 so as to block entry of any contaminants into test chamber 77. In the examples, test chamber wall 86 may extend radially outward from outer surface 29 of sample-receiving chamber 33 to an outer edge 139 having a profile matching that of inner surface 131 of housing 85 which may include curved and flat portions. Outer edge 139 may be sealed with inner surface 131 of housing 85 to entirely close opening 133 of housing 85 and to seal test chamber 77 by any suitable means, such as sonic welding.

To provide a tight fit securing sample-receiving chamber 33 and casing 83 with respect to housing 85, end wall 91 of sample-receiving chamber 33, and distal end wall 121 of casing may also have the profile of test chamber wall 86 and may also extend to a respective outer edge 141, 143 having a profile matching that of inner surface 131 of housing 85 which may include curved and flat portions. Securement of edges 141, 143 to inner surface 131, for example by sonic welding, permanently joins casing 83 with housing 85.

As illustrated in the examples of FIGS. 1-2, 4-5, and 8, housing 85 may further include an opening 145 facing toward bottom side 115 of casing 83 and test panels 101, 103. Transparent panel 87 may be sealed across opening 145 to enable viewing of test panels 101, 103 and any indication 105-111 provided by test panels 101, 103 while test chamber 77 remains sealed avoiding adulteration of the assay by contaminants to thereby ensure an accurate assay.

Opening 145 provides a window through which a user can see test panels 101, 103. Window is intended to be an expansive term referring to structure enabling the user to see the results of the test panels 101, 103. It is to be understood that the window provided by opening 145 may be covered with a transparent panel 87, or may be uncovered. And, the window enabling a user to see the test panels 101, 103 could be provided by structure other than an opening. For example, a window could comprise an entirely transparent housing 85 or a transparent region of an otherwise opaque housing 85 through which the test panels 101, 103 could be could observed.

Certain test chamber 77 components internal to housing 85 will now be described in connection with FIGS. 4, 7 and 10-15.

Well 99 for receiving bodily fluid filtrate 11*a* flowing under pressure from filter 75 via fluid port 97 will first be described. In the examples, well 99 may be formed in-part by well cover 153 and in-part by casing 83. Well cover 153 may also secure test panels 101, 103 within casing 83 of test chamber 77.

In the embodiments, well cover 153 may be sized for securement within casing 83 and such securement may also secure test panels 101, 103 within casing 83. More specifically, side edges 155, 157 of well cover 153 may abut a respective casing side 117, 119. Distal end edge 159 of well cover 153 may abut distal end wall 121 of casing and proximal end edge 161 may abut inner side 113 of end wall 91. Printed circuit board 162 may overlie well cover 153. Printed circuit board 162 and well cover 153 may be, secured within casing 83 against casing seats 163, 165 and separating wall 167 by snaps, 169, 171, 173, 175 as illustrated in FIGS. 4 and 12-13. Snaps 169, 171, 173, 175 may clip onto a respective side edge 174, 176 of printed circuit board 162 to hold printed circuit board 162 and well cover 153 in place within casing 83 against seats 163, 165 and wall 167.

Separate lanes 177, 179 may be provided, each to receive and secure one test strip 101, 103. More specifically, casing bottom side 115, distal end wall 121, casing seats 163, 165 and casing separating wall 167 and well cover 153 define lanes 177, 179 with well cover 153 spaced sufficiently above casing bottom 115 to provide space to receive and confine a test panel 101, 103. In the examples, test panels 101, 103 lie on casing bottom side 115 in a separate lane 177, 179. The lanes 177, 179 may be sized such that test panels 101, 103 are secured against movement along casing bottom side 115. Advantageously, each lane 177, 179 and the barrier provided by separating wall 167 avoids cross contamination of the respective test panels 101, 103 with reagents on such test panels 101, 103. As another advantage, this arrangement allows assay device 10 to be pre-manufactured and supplied to the user as a closed unit with the selected test panels 101, 103 in place for use of the assay device 10 with the particular assay of interest.

Well cover 153 may further include first viewing ports 181, 183 entirely through well cover 153 each positioned to be over the respective test regions 185, 187 of a test panel 101, 103 so that the user can observe any indications 105, 107, 109, 111 produced (or not produced) by test panels 101, 103 as a result of the assay. In the examples, viewing ports 181, 183 have an oval or racetrack configuration to enable a larger portion of the test regions 185, 187 to be observed. Viewing ports 181, 183 may be further aligned with transparent panel 87.

Turning now to FIGS. 4, 7 and 10-13, exemplary well 99 may be formed in-part by well cover 153 and in-part by casing 83 when well cover 153 is in place within casing 83. In the examples, well 99 may be formed by inner side 113 of end wall 91 of casing 83 and by top 189 and distal end 191 walls of well cover 153. Proximal end edge 161 of well cover 153 may be affixed to inner side 113 of end wall 91, for example by sonic welding. Bottom side 115 of casing 83 provides a bottom for well 99 in the examples. Sample pad portions 193, 195 of test panels 101, 103 (i.e., the first ends of test panels 101, 103) may be within well 99 for purposes of contacting bodily fluid filtrate 11a as described herein.

An example of an onboard light source 81 capable of use with assay device 10 will now be described in connection with FIGS. 4, 7, 10-11B and 14-16. Light source 81 may be considered onboard in that it is a part of assay device 10 rather than a component separate from assay device 10.

In the examples, light source 81 may comprise a pair of LED lamps 199, 201 capable of enhancing and amplifying indications 105, 107, 109, 111 provided by test panels 101, 103. Light source 81 improves visualization of the indications 105, 107, 109, 111 of the test panels 101, 103. Advantageously, light source 81 allows a user to easily, observe what might otherwise be near-imperceptible indications 105, 107, 109, 111 provided by test panels 101, 103 such as can occur at an early point in time during an assay or when trace amounts of analytes are present. Such small changes might otherwise be incapable of being observed with a naked human eye. Provision of light source 81 onboard assay device 10 means that assay device 10 may be a self-contained, user-friendly unit fully capable of use without any external systems or components. Therefore, light source 81 provides an opportunity to provide better information faster, enabling earlier and more accurate diagnoses using assay device 10.

In the examples, light source 81 may be a component of printed circuit board 162. Printed circuit board 162, light source 81 and related circuitry on printed circuit board 162 may be covered by housing 85, and fully within test chamber 77. As previously described, printed circuit board 162 may be held in place within casing 83 by snaps 169, 171, 173, 175 and printed circuit board 162 may hold well cover 153 thereby holding test panels 101, 103 in lanes 177, 179

In addition to lamps 199, 201, other components mounted on printed circuit board 162 can include microswitch 203, a power source consisting of a pair of batteries 205, 207 and a circuit connecting lamps 199, 201, microswitch 203, and batteries 205, 207.

A slide 209 may be provided to automatically close microswitch 203 to energize light source 81 when fluid sample collector 13 is fully coupled to assessment unit 15. In such examples, slide 209 would not contact microswitch 203 when sample collector 13 is at positions other than being fully seated on assessment unit 15 so that microswitch 203 is open and light source 81 is not energized. Therefore, assay device 10 may be supplied to the user as a closed contaminant-free unit with cap 17 partially coupled to sample-receiving chamber 33 and light source 81 in an "off" state.

Slide 209 may include a generally U-shaped follower portion 211 and arm 213. As illustrated in FIG. 14, follower 211 may slide axially in the direction of arrow 95 on tubular outer surface 29 of sample-receiving chamber 33 with proximal end 217 of arm 213 in slot 219 in test chamber wall 86 and distal end 221 of arm 213 in slot 223 provided in sample-receiving chamber 33 end wall 91. The coaction of slots 219, 223 and arm 213 limits rotational movement of follower 211 around outer surface 29.

Rotation of cap 17 on assessment unit 15 in the direction of arrow 96 with threads 23, 27 meshed together causes cap 17 to advance in the direction of axial arrow 95. Axial advancement of cap 17 on outer surface 29 of sample-receiving chamber 33 brings inner edge 224 of cap 17 into contact with proximal end of 217 of arm 213 urging slide 209 in the direction of arrow 95. Tip 225 of arm 213 presses against a contact 227 of microswitch 203 when slide 209 moves fully in the direction of arrow 95 to close microswitch 203 and energize lamps 199, 201 to an "on" position to provide light energy 231 schematically illustrated in FIGS. 15-16. By way of example only, if cap 17 is capable of 30 mm axial travel in the direction of arrow 95, then movement to the cap 17 by a 30 mm distance causes slide 209 arm 213 to contact and close microswitch 203 activating light source 81.

Referring to FIGS. 4, 7, 10, and 14-15, lamps 199, 201 may be supported on a lamp mount 229. Lamps 199, 201 may include a lamp axis 230 (FIG. 10) along which a majority of light energy 231 is emitted. Lamps 199, 201 may be mounted on lamp mount 229 with lamp axis 230 at an angle relative to a plane 233 defined by test panels 101, 103 located in lanes 177, 179. As illustrated in FIG. 10, the angle of lamp axis 216 relative to plane 233 may be between about 30° to about 50° with an angle of about 45° being desirable in terms of delivery of ample light energy 231 toward test panels 101. 103.

Printed circuit board 162 may be parallel to plane 233. Lamps 199, 201 may be aimed to project light energy 231 through second viewing ports 235, 237 provided entirely through printed circuit board 162 and onto test panels 101, 103. In the examples, second viewing ports 235, 237 may align with first viewing ports 181, 183 and the location of test regions 185, 187 of test panels 101, 103. The alignment enables light energy from lamps 199, 201 to strike test panels 101, 103. The alignment further enables a user to look through transparent panel 87 and first and second viewing ports 181, 183, 235, 237 to see test regions 185, 187 and any indications 105-111 thereon (or lack of such indications) as illuminated by light energy from lamps 199, 201.

Lamps 199, 201 may be light emitting diode (LED) lamps and may be selected to have a wattage of about 10 watts to about 40 watts, although the exact type and power of lamp 199, 201 may be selected based on the application of assay device 10. Batteries 205, 207 powering lamps 199, 201 may each be a 3 volt coin cell, such as a CR1025 coin cell.

Lamps 199, 201 of light source 81 may emit ultra violet (UV) light energy with wavelengths in the range of about 200 nm to about 350 nm. In other examples, lamps 199, 201 could emit light energy both within and outside the UV light spectrum, for instance, a light energy range of about 350 nm to about 450 nm may be implemented. In still other examples, light energy outside the UV range (e.g., visible light exceeding 400 nm) may be emitted. The light energy emitted in any particular embodiment of assay device 10 may be chosen to meet the particular purpose of the assay device 10. Light source 81 may, for example, improve visualization of indications 105, 107, 109, 111 by causing fluorescence of a label associated with the analyte such that the fluorescence can be detected with a human eye and the fluorescence provides the result of the assay.

Light source 81 provides an opportunity for important advantages. One advantage of light source 81 is that it enables viewing of an indication 105, 107, 109, 111 at the earliest possible time following the start of the assay. As is known, the indication produced by a LFSA type test panel 101, 103 may intensify as the amount of detected analyte increases, transitioning from a faint indication to a potentially intense indication. Light source 81 provides an opportunity to detect any indication rapidly once it occurs. Getting an indication quickly could be important, for example, when attempting to determine whether an athlete has sustained a concussion during a sporting event. Getting a rapid result can determine whether the athlete needs immediate medical attention or can be returned to the event.

Another advantage of light source 81 is that the light energy 231 may improve visualization of weak indications 105, 107, 109, 111 provided by test panels 101, 103 when concentrations of analyte are at trace or low concentration levels. Light source 81 may enable identification of analyte concentrations of less than about 1 picogram of analyte per milliliter of filtrate 11a (1 µg analyte/ml filtrate). Analyte concentrations at trace levels of 1 pg/ml would cause test panels 101, 103 to provide indications 105, 107 that would be essentially imperceptible to the naked human eye without light source 81.

As yet another advantage, light source 81 of assay device 10 may improve visualization of indications 105, 107, 109, 111 provided by some test panels 101, 103 at analyte concentrations selected as "cutoff" values. A cutoff value represents a predetermined threshold concentration level of analyte indicative of a condition for which the assay device 10 is designed to detect. An indication 105, 107 or 109, 111 occurs when the analyte is present in sufficient amount to meet or exceed the cutoff value. The indication is binary; it exists or it does not exist. Light source 81 enables observation of the cutoff value indication positively and with confidence. By way of example only, separate test panels (e.g., test panel 101 or 103) could have cutoff values of 11 pg/ml for a first analyte or 500 ng/ml for a second and different analyte respectively indicating that an assay may be constructed to have sensitivity to different analyte concentrations as could be necessary for detection of a particular condition in a subject.

In embodiments, the coupling of fluid sample collector 13 to assessment unit 15 both seals a bodily fluid 11 sample within assessment unit 15 and may activate light source 81 providing a hygienic and self-contained sample-receiving chamber 33 and test chamber 77 in which the assay result can be easily visualized. As already described, engagement of connecting and receiving threads 23, 27 advances cap 17 and plunger 19 in the direction of arrow 95 when cap 17 is rotated in the direction of arrow 96. Engagement of threads 23, 27 couples cap 17 of fluid collector 13 to assessment unit 15 in the examples. Advancement of plunger 19 within the close walls of sample-receiving chamber 33 causes a pressure increase within sample-receiving chamber 33 as plunger 17 advances. As a result, pressure on the side of filter 75 facing sample-receiving chamber 33 is greater than pressure on the side of filter 75 facing test chamber 77 causing bodily, fluid 11 to flow through filter 75 whereupon particles greater than the pore 100 size are blocked by filter 75. Compression of absorbent member 21 further increases pressure within sample-receiving chamber 33 also causing bodily fluid 11 to flow through filter 75. Filtrate 11a from filter 75 with impurities and particles larger than the pore 100 size removed flows through port 97 and into well 99. Once cap 17 is fully advanced in the direction of arrow 95, contact between cap 17 and slide 209 may advance arm 213 tip 225 to touch contact 227 and to close microswitch 203 to activate lamps 199, 201. Lamps 199, 201 generate light energy 231 enabling improved visualization of test panels 101, 103 and any indication 105, 107, 109, 111 provided by test panels 101, 103 as a result of an assay. Because assay device 10 may be a single use disposable device, there is no need to provide a position deactivating light source 81. However, reverse rotation of cap 17 would have the effect of opening microswitch 203 to deactivate light source 81.

Referring to FIGS. 4, 7, and 10-16, examples of test panels 101, 103 will next be described. As previously stated, test panels 101, 103 may be of an LISA type. Analytes which may be detected with test panels 101, 103 of assay device 10 may include any molecule or target of interest, such as proteins, carbohydrates, nucleic acids, and ribonucleic acids which may be present in bodily fluid 11. In embodiments, each test panel 101, 103 may be constructed to identify a specific and different analyte. Providing a test panel 101, 103 targeted to a specific analyte enables assay device 10 to identify the existence of plural analytes which may be more predictive of an abnormal condition than identification of a single analyte. Greater specificity may be provided by implementation of three, four, or more test panels. In still other embodiments, test panels 101, 103 may each be constructed to identify plural analytes. Assay device 10 is capable of customization to accommodate test panels 101, 103 or other assay devices as required by the user.

Assay device 10 of the examples may include test panels 101, 103 in the form of separate lateral flow strip assays, each specific to one biomarker. Providing two separate test panels 101, 103 eliminates the potential for crossover and contamination between different reagents on the same test panel. Provision of separate lanes 177, 179 with separating wall 167 between portions of test panels 101, 103 with reagents on them further avoids risk of cross contamination between the reagents of the test panels 101, 103.

Referring to FIGS. 12 and 13, each LFSA-type test panel 101, 103 may be a series of capillary beds (i.e., pads), comprised of materials such as porous paper, microstructured polymer, and sintered polymer. Each panel 101, 103 has the capacity to transport bodily fluid filtrate 11a spontaneously. The transfer of filtrate 11a across the test panel 101, 103 is by diffusion, or wicking, rather than by pressurized fluid flow. Each test panel 101, 103 may include a sample pad 193, 195, a conjugate pad 239, 241, a nitrocellulose membrane pad 243, 245, a test region 185, 187, and an absorbent pad 247, 249.

Each sample pad 193 may be at a first or proximal end of the test panel 101, 103 and may extend into well 99 where bodily fluid filtrate 11a contacts sample pad 193, 195. Bodily fluid filtrate 11a then diffuses along test panel 101, 103 to conjugate pad 239, 241. At conjugate pad 239, 241 labeled antibodies specific to the target analyte bind to analyte in bodily fluid filtrate 11a if the analyte is present. The antibodies may be tagged with any suitable labels. Examples of labels are colloidal metals such as gold or silver, carbon, visible or florescent dyes, magnetic particles, enzymes, latex beads, or a combination of these labels. The labels result in the indication 105, 107 at test region 185, 187, which can be seen with the human eye especially when excited by light energy 231 from light source 81.

Figure 16:
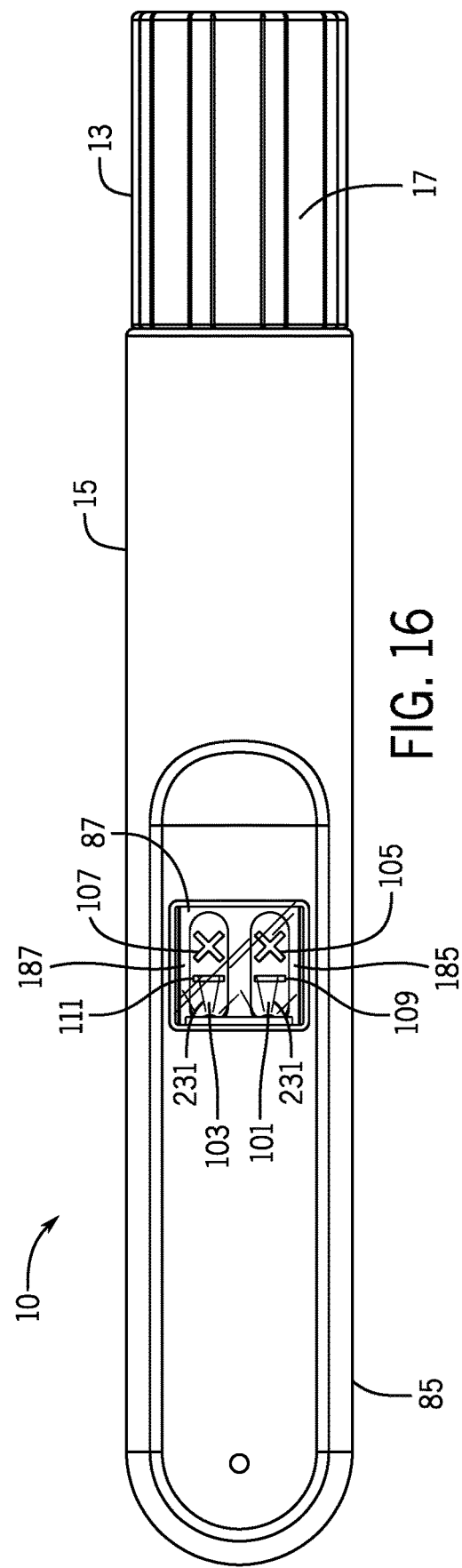
FIG. 16 illustrates the assay device of FIG. 1 showing indications indicative of a "positive" assay both with respect to analyte detection and sufficiency of bodily fluid.

In test region 185, 187, test 251, 253 and control 255, 257 lines of binding reagents are drawn on the nitrocellulose membrane. As the bodily fluid filtrate 11a continues to migrate along test panel 101, 103 in lanes 177, 179 toward the second or distal end of test panel 101, 103, the binding of those reagents to the target analyte will result in the appearance of a line or some other predetermined symbol. In the examples of FIGS. 13 and 15-16, an X-shaped symbol ("X") 105, 107 may appear, but any suitable indicia may be implemented. Intensity of the color at test lines 251, 253 corresponds to the amount of target analyte and can be seen visually if sufficient analyte is present.

Referring further to FIGS. 13 and 15-16, control lines 255, 257 may be provided past test lines 251, 253. In embodiments, antibodies specific to the label released from conjugate pad 239, 241 are bound to test panel 101, 103 at control lines 255, 257. Bodily fluid filtrate 11a releases label (and its bound antibody) in excess of that bound to analyte and carries the label to control lines 255, 257. Binding of label to conjugate antibodies at control lines 255, 257 indicates that a sufficient volumetric amount of bodily fluid filtrate 11a is present to consider the assay to be valid. In the examples, a bar-shaped symbol ("-") 109, 111 appears, but any suitable indicia may be implemented. Intensity of the appearance of bar-shaped symbol 109, 111 at control lines 255, 257 corresponds to the amount of excess label indicative of sufficient volumetric amounts of bodily fluid filtrate 11a and can be seen visually if sufficient label is present. FIG. 16 illustrates lamps 199, 201 in an "on" state generating light energy 231. FIG. 16 further shows indications 105, 107, 109, 111 excited by light energy 231 as being clearly visible to a user through transparent panel 87 even if only trace amounts of analyte are present in the bodily fluid sample 11 or at early stages of the assay.

Absorbent pad 247, 249 toward distal end of test panels 101, 103 is designed to absorb excess amounts of bodily fluid filtrate 11a. Absorbent pad 247, 249 helps in maintaining the flow rate of bodily fluid filtrate 11a and helps stop any back flow of such filtrate 11a. The specification of absorbent pad 247, 249 will have an impact on the volume of bodily fluid 11a that the test can incorporate.

Operation of exemplary assay device 10 and a method of conducting an assay will now be described in connection with FIGS. 1-16. Assay device 10 may be initially provided in the form of a self-contained unit with fluid sample collector 13 coupled to assessment unit 15 as illustrated in FIG. 1. As such, assay device 10 is a type of assay system and/or assay kit. Sample collector 13 may be coupled to assessment unit 15 sufficiently to close sample-receiving chamber 33 while not activating light source 81. This enables assay device 10 to be supplied in a ready-to-use condition. Providing assay device 10 to a user with sample collector 13 coupled to assessment unit 15 further provides an opportunity for absorbent member 21, sample-receiving chamber 33, and test chamber 77 to be in a clean, hygienic state or even a sterile state prior to use which is desirable to ensure the validity of the assay. Further, assay device 10 may be provided to the user in a sealed container, such as a bag, in a hygienic or completely sterile condition prior to use.

Assay device 10 may be of lightweight plastic materials making it easily portable for use in a broad range of settings, such as a component of a medical first aid kit.

When an assay of a type capable of being performed by the particular assay device 10 is desired, cap 17 of fluid sample collector 13 may be completely decoupled from assessment unit 15 in a simple and intuitive manner. Cap 17 may simply be rotated counterclockwise (opposite that of arrow 96) with the user's fingers to accomplish the decoupling. Cap 17, plunger 19, and absorbent member 21 may then be moved axially along sample-collector axis 43 to separate fluid sample collector 13 from assessment unit 15.

If a saliva sample is to be assayed, the user may then place absorbent member 21 directly in the subject's mouth to drench absorbent member 21 with saliva. Alternatively, absorbent member 21 may be dipped in a vessel containing a saliva sample of interest. If provided, moisture indicator 47 on plunger 19 will provide an indication of a state change (e.g., a color change) as illustrated in FIG. 2A if sufficient moisture is present on absorbent member 21 to proceed with the assay. Collection of a urine sample or another bodily fluid sample 11 may be conducted in much the same way.

The user may then couple the fluid sample collector 13 to the assessment unit 15 in a manner which is also highly intuitive. Specifically, the user simply inserts plunger 19 and absorbent member 21 axially into sample-receiving chamber 33 in the direction of arrow 95 along sample-collector and chamber axes 43, 94 until threads 23, 27 come into contact. Cap 17 is then be rotated on threads 23, 27 in a clockwise direction 96 to couple together the fluid sample collector 13 and assessment unit 15 into a single closed unit. The elegant design of assay device 10 essentially "informs" the user with respect to how to uncouple, recouple, and use the device.

In the examples, rotation of cap 17 of fluid sample collector 13 on threads 23, 27 causes axial advancement of cap 17, plunger 19 carried by cap 17, and absorbent member 21 into sample-receiving chamber 33 along axis 43 in the direction of arrow 95. Cap 17 may rotate independent of plunger 19. Axial advancement of plunger 19 during rotation of cap 17 creates a pressure within sample-receiving chamber 33 of about 40 kPa to about 200 kPa, a pressure range of about 5.8 PSI to about 29 PSI as plunger 19 moves in the direction of arrow 95.

The pressure increase within sample-receiving chamber 33 causes bodily fluid 11 to flow through filter 75, port 97, and into well 99. The pressure created may be without excessive peak pressures because rotation of cap 17 on mating threads 23, 27 to advance plunger 19 is more gradual with forward axial motion of plunger 19 within sample-receiving chamber 33 being controlled by the pitch of the mating threads 23, 27, particularly when compared with a thrusting-type motion provided with a syringe-type plunger. In addition, the action of threads 23, 27 easily provides a mechanical advantage allowing sufficient fluid pressure to build within sample-receiving chamber 33 to drive bodily fluid 11 from absorbent member 21, through filter 75, port 97, and into well 99.

Without wishing to be bound by any particular theory, the pressure provided by controlled advancement of plunger 19 is thought to result in improved filtration of bodily fluid 11 and improved removal of contaminants (e.g., food, mucous, etc.) to provide a highly purified filtrate 11a. More extreme and rapid pressure build-up is thought to result in contaminants being driven through filter 75 resulting in a less pure filtrate 11a and potentially adulterating the assay. The pressure generated by axial advancement of plunger 19 along axis 43 within sample-receiving chamber 33 by the process of coupling of fluid collector 13 with assessment unit 15 is sufficient to quickly deliver bodily fluid 11 through filter 75 and to well 99 and test panels 101, 103, thereby reducing the time required to perform an assay and providing a faster result as compared with an assay that relies solely on movement of bodily fluid 11 through a diffusion or wicking process.

Coupling of fluid sample collector 13 with assessment unit 15 may also serve to activate light source 81 making viewing of any indications 105, 107, 109, 111 on the test panels 101, 103 easier and improving confidence in the assay result. In the examples, the coupling of rotation of cap 17 and axial advancement of cap 17 on assessment unit 15 advances cap 17 and slide 209 in the direction of arrow 95. In the examples, advancement of cap 17 on assessment unit 15 causes inner edge of cap 224 to eventually contact proximal end 217 of arm 213 to urge slide 209 tip 225 to push contact 227 of microswitch 203 closing switch 203 and activating light source 81 and lamps 199, 201. In the examples, microswitch 203 may be closed when cap 17 reaches its maximum travel to complete the coupling process of fluid collector 13 and assessment unit 15. Lamps 199, 201 may remain activated until batteries 205, 207 are depleted or until cap 17 is moved in a direction opposite arrow 95. Assay device 10 flattened bottom portions 39, 41 may then be placed on a flat surface during performance of the assay.

Filtrate 11a in well 99 may contact sample pad portion 193, 195 of test panels 101, 103. Filtrate 11a then wicks through test panels 101, 103 past conjugate pad 239, 241 whereupon analyte is conjugated by a labeled antibody and excess unbound labeled antibodies are released from conjugate pad 239, 241. Conjugated analyte and unbound labeled antibodies are wicked further along test panels 101, 103 to test regions 185, 187 of nitrocellulose pad 243, 245. Antibodies on test line 251, 253 bind with analytes to produce X-shaped indications 105, 107 in the examples. If analytes targeted by each test panel 101, 103 are present, then both indications 105, 107 will appear. If one analyte targeted by one test panel 101, 103 is present but the other analyte is not present, then one indication 105 or 107 will appear. If neither analyte is present, then neither indication 105, 107 will appear.

If sufficient fluid filtrate 11a is present on test panel 101, 103, then unbound label will become conjugated to antibodies on control lines 255, 257 to provide separate bar-shaped indications 109, 111 in the example. The presence of each bar-shaped indication 109, 111 provides confidence that the assay was conducted correctly with sufficient volumetric amounts of bodily fluid 11 to ensure the presence of each analyte of interest. The absence of bar-shaped indication 109, 111 is indicative that insufficient filtrate 11a was present to have confidence that analyte may be present in the sample. FIG. 16 is representative of an assay device 10 with two test panels 101, 103 and with positive X-shaped indications 105, 107 for each analyte and with positive bar-shaped indications indicative that sufficient filtrate 11a was present on test panels 101, 103.

Lamps 199, 201 of light source 81 emit energy, which may be UV light energy, to excite the label associated with analyte bound at test and control lines 251, 253, 255, 257. For example, light energy 81 may cause fluorescence of a label associated with the analyte. Therefore, light source 81 improves visualization of the indications 105, 107, 109, 111 provided by test panels 101, 103 enabling a user to more positively see even very weak indications provided by trace amounts of analytes down to analyte concentrations of about 0.1 pg/ml.

Assay device 10 advantageously provides an elegant and intuitive device, system, kit, and method with which to collect a bodily fluid sample 11, filter and purify the sample 11, and test for the existence of one or more analyte of interest. Bodily fluid 11 transfer from sample collector 13 to assessment unit 15 and test panels 101, 103 is rapid as a result of the positive displacement device embodied by advancement of plunger 19 and absorbent member 21 within sample-receiving chamber 33. The assay result, such as in the form of indications 105, 107, 109, 111, may be viewable directly through transparent panel 87.

Light source 81 may be provided to enable indications 105, 107, 109, 111 to be identified at the earliest possible time after commencement of the assay and with confidence. Light source 81 of the examples, is conveniently a part of assay device 10 avoiding any need for a separate source of light energy. In addition, light source 81 may be automatically activated by the intuitive coupling of fluid sample collector 13 with assessment unit 15 during the bodily fluid transfer process providing the best possible opportunity for the user to immediately visualize the result of the assay at the earliest possible time.

As already stated, assay device 10 may be made of lightweight materials that are inexpensive to make, for example by plastic injection molding. The lightweight makes handling and use easy. The opportunity to provide a low-cost assay device 10 enables assay device 10 to be discarded after a single-use if that is desired. Assay devices 10 and the method of use provides information to a user enabling better healthcare results.

The foregoing description is provided for the purpose of explanation and is not to be construed as limiting the invention. While the invention has been described with reference to preferred embodiments or preferred methods, it is to be understood that the words which have been used herein are words of description and illustration, rather than words of limitation. Section headings are non-limiting and are provided for the reader's convenience only. Furthermore, although the invention has been described herein with reference to particular structure, methods, and embodiments, the invention is not intended to be limited to the particulars disclosed herein, as the invention extends to all structures, methods and uses that are within the scope of the appended claims. The disclosed assay devices may address some or all of the problems previously described.

A particular embodiment need not address all of the problems described, and the claimed assay devices should not be limited to embodiments comprising solutions to all of these problems. Further, several advantages have been described that flow from the structure and methods; the present invention is not limited to structure and methods that encompass any or all of these advantages. Those skilled in the relevant art, having the benefit of the teachings of this specification, may effect numerous modifications to the invention as described herein, and changes can be made without departing from the scope and spirit of the invention as defined by the appended claims. Furthermore, any features of one described embodiment can be applicable to the other embodiments described herein.

What is claimed is:

1. An assay device for detection of an analyte in a bodily fluid sample, the assay device comprising:
    a fluid sample collector, including:
        a cap;

a plunger carried by the cap and having a distal end;
an absorbent member supported toward the distal end of the plunger; and
an assessment unit to which the fluid sample collector couples, including:
  a sample-receiving chamber having at least one sidewall, a fluid outlet, and an opening through which the plunger and absorbent member are received within the sample-receiving chamber, the plunger and the at least one sidewall being closely sized such that pressure is increased within the sample-receiving chamber as the plunger is advanced toward the outlet;
  a fluid filter across the outlet;
  a well in fluid communication with the outlet to receive fluid sample filtrate therefrom;
  at least one test panel in fluid communication with the well, the at least one test panel providing an indication when contacted by an analyte in the filtrate;
  helical threads on the cap and the assessment unit which removably couple the cap to the assessment unit closing the opening, the threads further having a pitch converting rotational force to linear force to advance the plunger axially within the sample-receiving chamber as the cap is rotated to create a differential pressure across the filter driving the fluid sample therethrough and the filtrate into the well, the axial advancement of the plunger being controlled by the pitch of the threads; and
  a window through which the indication is viewed.

2. The assay device of claim 1 wherein the sample-receiving chamber further includes an end wall, the outlet is a port through the end wall, and the filter is across the port.

3. The assay device of claim 2 wherein the filter has a pore size of about 0.1 μm (micron) to about 120 μm (micron).

4. The assay device of claim 3 wherein the filter is selected from the group consisting of a hydrophilic membrane, a hydrophobic membrane, and combinations thereof.

5. The assay device of claim 3 wherein the plunger and the sample-receiving chamber each define an axis and the plunger and absorbent member are inserted into the sample-receiving chamber such that the axes are coaxial.

6. The assay device of claim 5 wherein rotation of the cap on the threads axially advances the plunger to compress the absorbent member and express the bodily fluid therefrom.

7. The assay device of claim 6 wherein the absorbent member is a sponge.

8. The assay device of claim 6 wherein the fluid sample collector further includes a moisture indicator in fluid communication with the absorbent member which produces an indication when contacted by a volume of fluid sufficient for testing with the assay device.

9. The assay device of claim 6 wherein the axial advancement of the plunger creates a pressure within the sample-receiving chamber of about 40 kPa (Kilopascal) to about 200 kPa (Kilopascal).

10. The assay device of claim 1 further including a light source within the assessment unit configured to provide visualization of the indication through the window.

11. The assay device of claim 10 wherein the rotation of the cap on the threads axially advances the cap to activate the light source.

12. The assay device of claim 11 wherein the light source causes fluorescence of a label associated with the analyte.

13. The assay device of claim 12 wherein the assessment unit further includes:
  a housing including the window, the fluid filter, the well, and the at least one test panel being in the housing with each test panel being viewable through the window; and
  a test chamber within the housing, and the well and the at least one test panel are within the test chamber.

14. The assay device of claim 13 wherein the assessment unit further includes an on/off switch for the light source which is closed to activate the light source by axial advancement of the cap, wherein both the light source and switch are within the housing.

15. The assay device of claim 14 further including a power source and the light source, switch, and power source are components on a printed circuit board within the housing.

16. The assay device of claim 14 wherein the light source is at an angle relative to the at least one test panel.

17. The assay device of claim 16 wherein the light source is at an angle of about 30° to about 50° relative to the at least one test panel.

18. The assay device of claim 11 wherein the light source emits at least ultra violet (UV) light.

19. The assay device of claim 18 wherein the light emitted by the light source is in the range of about 200 nm to about 350 nm.

20. The assay device of claim 18 wherein the light source improves visualization of the indication at analyte concentrations of about 0.1 picogram of analyte per 1 milliliter of filtrate (1 pg analyte/ml filtrate) or greater.

21. The assay device of claim 11 wherein the test panel is a first test panel which produces a first indication when contacted by a first analyte and the assessment unit further includes a second test panel in fluid communication with the well which produces a second indication when contacted by a second analyte in the fluid filtrate.

22. The assay device of claim 21 wherein each indication is a symbol on the test panel.

23. The assay device of claim 22 wherein each test panel produces a further indication indicative of contact by a sufficient volume of fluid filtrate to ensure an accurate assay.

24. The assay device of claim 23 wherein each test panel is of a material which wicks the fluid filtrate from the well.

25. The assay device of claim 11 wherein the assay device is a single-use disposable device.

26. The assay device of claim 25 wherein the assay device is supplied for the single-use with the fluid sample collector coupled to the assessment unit.

* * * * *